US011078473B2

(12) United States Patent
Chou et al.

(10) Patent No.: US 11,078,473 B2
(45) Date of Patent: Aug. 3, 2021

(54) LYSINE DECARBOXYLASES HAVING MODIFICATIONS AT TITRATABLE AMINO ACIDS

(71) Applicants: CATHAY BIOTECH INC., Shanghai (CN); CIBT AMERICA INC., Newark, DE (US)

(72) Inventors: Howard Chou, Shanghai (CN); Ling Chen, Shanghai (CN); Wenqiang Lu, Shanghai (CN); Xiucai Liu, Shanghai (CN)

(73) Assignees: CATHAY BIOTECH INC., Shanghai (CN); CIBT AMERICA INC., Newark, DE (US)

( * ) Notice: Subject to any disclaimer, the term of this patent is extended or adjusted under 35 U.S.C. 154(b) by 0 days.

(21) Appl. No.: 16/473,215

(22) PCT Filed: Dec. 30, 2016

(86) PCT No.: PCT/CN2016/113516
§ 371 (c)(1),
(2) Date: Jun. 24, 2019

(87) PCT Pub. No.: WO2018/120025
PCT Pub. Date: Jul. 5, 2018

(65) Prior Publication Data
US 2019/0330614 A1 Oct. 31, 2019

(51) Int. Cl.
*C12N 9/88* (2006.01)
*C12P 13/00* (2006.01)

(52) U.S. Cl.
CPC .............. *C12N 9/88* (2013.01); *C12P 13/001* (2013.01); *C12Y 401/01018* (2013.01)

(58) Field of Classification Search
None
See application file for complete search history.

(56) References Cited

U.S. PATENT DOCUMENTS

| 6,610,836 B1 * | 8/2003 | Breton | C07K 14/26 435/320.1 |
| 9,765,369 B2 * | 9/2017 | Mochizuki | C12N 9/88 |
| 2011/0039313 A1 * | 2/2011 | Verseck | C12P 13/001 435/128 |
| 2012/0295317 A1 * | 11/2012 | Schroder | C12P 13/001 435/128 |

FOREIGN PATENT DOCUMENTS

| CN | 104498519 A | 4/2015 |
| EP | 1482055 A1 | 12/2004 |
| EP | 2806026 A1 | 11/2014 |
| WO | 2008142034 A2 | 11/2008 |
| WO | 2008142034 A3 | 11/2008 |
| WO | 2015196430 A1 | 12/2015 |
| WO | 2016119230 A1 | 8/2016 |
| WO | WO-2016129812 A1 * | 8/2016 | .............. C12P 13/00 |

OTHER PUBLICATIONS

NCBI Blast Protein Alignment Seq ID No. 11 of WO 2016/129812 PDF Printout (Year: 2020).*
NCBI Blast Protein Alignment Seq ID No. 130001 of U.S. Pat. No. 6,610,836 PDF Printout (Year: 2020).*
International Search Report issued in Application No. PCT/CN2016/113516 dated Oct. 13, 2017, 4 pages.
Puzio, P. et al. "unnamed protein product [Hafnia alvei]" retrieved from NCBI GenBank accession No. CAV25914.1, Dec. 17, 2008 (Dec. 17, 2008), 2 pages.
Breton, G. L. et al. "Sequence 13001 from U.S. Pat. No. 6,610,836" retrieved from NCBI GenBank accession No. AAR53284.1, Dec. 18, 2003 (Dec. 18, 2003), 1page.
Plesch , G. et al. "unnamed protein product[*Salmonella enterica* subsp. *enterica* serovar *Typhi*]" retrieved from NCBI GenBank accession No. CBA1102.1, Jul. 28, 2009 (Jul. 28, 2009), 1 page.
Puzio, P. et al. "unnamed protein product [Vibrio parahaemolyticus]" retrieved from NCBI GenBank accession No. CBG 14132.1, Sep. 25, 2009 (Sep. 25, 2009), 1 page.
Plesch, G. et al. "unnamed protein product [Vibrio parahaemolyticus]" retrieved from NCBI GenBank accession No. CBA11249.1, Jul. 28, 2009 (Jul. 28, 2009), 2 pages.
Plesch, G. et al. "unnamed protein product [Vibrio vulnificus]" retrieved from NCBI GenBank accession No. CBA11215.1, Jul. 28, 2009 (Jul. 28, 2009), 1 page.
Plesch, G. et al. "unnamed protein product [Vibrio cholerae]" retreived from NCBI GenBank accession No. CBAI 1206.1, Jul. 28, 2009 (Jul. 28, 2009), 1 page.
Puzio, P. et al. "unnamed protein product [Vibrio vulnificua]" retrieved from NCBI GenBank accession No. CBG 14138.1, Sep. 25, 2009 (Sep. 25, 2009), 2 pages.
Plesch, G. et al. "unnamed protein product [Moritella japonica]" retrieved from NCBI GenBank accession No. CBA11214.1, Jul. 28, 2009 (Jul. 28, 2009), 2 pages.
Sequence 9425 from Patent WO 2008142034-A2, Nov. 27, 2008, pp. 1-2.
Supplementary European Search Report issued in corresponding EP Patent Application No. EP 16925168.3, dated Oct. 12, 2020 (7 pages).

* cited by examiner

*Primary Examiner* — Anand U Desai
(74) *Attorney, Agent, or Firm* — Rothwell, Figg, Ernst & Manbeck, P.C.

(57) ABSTRACT

The invention provides CadA polypeptides with mutations that increase activity in alkaline pH compared to the wild-type lysine decarboxylase. The invention also provides methods of generating such mutant polypeptides, microorganisms genetically modified to overexpress the mutant polypeptides, and methods of generating such microorganisms.

14 Claims, 2 Drawing Sheets

Specification includes a Sequence Listing.

Figure 1

```
SALMONELLA_ENTERICA_WP_001540636.1            MNVIAIMNHMGVYFKEEPIRELHRALEGLNFRIVYPNDREDLLKLIENNSRLCGVIFDWD
ESCHERICHIA_MULTISPECIES_CADA                 MNVIAILNHMGVYFKEEPIRELHRALERLNFQIVYPNDRDDLLKLIENNARLCGVIFDWD
KLEBSIELLA_MULTISPECIES_WP_012968785          MNVIAIMNHMGVYFKEEPIRELHRALERLDFRIVYPNDRDDLLKLIENNSRLCGVIFDWD
ENTEROBACTERIAECEAE_MULTISPECIES_WP_002892486.1 MNVIAIMNHMGVYFKEEPIRELHRALERLDFRIVYPNDRDDLLKLIENNSRLCGVIFDWD
                                              ******:.:*********************:*:.*********:************

SALMONELLA_ENTERICA_WP_001540636.1            KYNLELCEEISKLNEYMPLYAFANSYSTLDVSLNDLRMQVRFFEYALGAATDIAAKIRQN
ESCHERICHIA_MULTISPECIES_CADA                 KYNLELCEEISKMNENLPLYAFANTYSTLDVSLNDLRLQISFFEYALGAAEDIANKIKQT
KLEBSIELLA_MULTISPECIES_WP_012968785          KYNLELCEEISKMNEYMPLYAFANTYSTLDVSLNDLRMQVRFFEYALGAAEDIANKIKQN
ENTEROBACTERIAECEAE_MULTISPECIES_WP_002892486.1 KYNLELCEEISKMNEYMPLYAFANTYSTLDVSLNDLRMQVRFFEYALGAAEDIANKIKQN
                                              ************:**:*.*****:********:**.:*********:***:**:*

SALMONELLA_ENTERICA_WP_001540636.1            TDEYIDNILPPLTKALFKYVREGKYTFCTPGHMGGTAFQKSPVGSIFYDFFGPNTMKSDI
ESCHERICHIA_MULTISPECIES_CADA                 TDEYINTILPPLTKALFKYVREGKYTFCTPGHMGGTAFQKSPVGSLFYDFFGPNTMKSDI
KLEBSIELLA_MULTISPECIES_WP_012968785          TDEYIDTILPPLTKALFKYVREGKYTFCTPGHMGGTAFQKSPVGSIFYDFFGPNTMKSDI
ENTEROBACTERIAECEAE_MULTISPECIES_WP_002892486.1 TDEYIDTILPPLTKALFKYVREGKYTFCTPGHMGGTAFQKSPVGSIFYDFFGSNTMKSDI
                                              ****:..:****************************************:*********

SALMONELLA_ENTERICA_WP_001540636.1            SISVSELGSLLDHSGPHKEAEEYIARVFNAERSYMVTNGTSTANKIVGMYSAPAGSTVLI
ESCHERICHIA_MULTISPECIES_CADA                 SISVSELGSLLDHSGPHKEAEQYIARVFNADRSYMVTNGTSTANKIVGMYSAPAGSTLLI
KLEBSIELLA_MULTISPECIES_WP_012968785          SISVSELGSLLDHSGPHKEAEEYIARVFNAERSYMVTNGTSTANKIVGMYSAPAGSTVLI
ENTEROBACTERIAECEAE_MULTISPECIES_WP_002892486.1 SISVSELGSLLDHSGPHKEAEEYIARVFNAERSYMVTNGTSTANKIVGMYSAPAGSTVLI
                                              *********************:*******:*****************************:**

SALMONELLA_ENTERICA_WP_001540636.1            DRNCHKSLTHLMMMSDITPIYFRPTRNAYGILGGIPQSEFQHATIAKRVKETPNATWPVH
ESCHERICHIA_MULTISPECIES_CADA                 DRNCHKSLTHLMMMSDVTPIYFRPTRNAYGILGGIPQSEFQHATIAKRVKETPNATWPVH
KLEBSIELLA_MULTISPECIES_WP_012968785          DRNCHKSLTHLMMMSDITPIYFRPTRNAYGILGGIPQSEFQHATIAKRVKETPNATWPVH
ENTEROBACTERIAECEAE_MULTISPECIES_WP_002892486.1 DRNCHKSLTHLMMMSDITPIYFRPTRNAYGILGGIPQSEFQHATIAKRVKETPNATWPVH
                                              ****************:*******************************************

SALMONELLA_ENTERICA_WP_001540636.1            AVITNSTYDGLLYNTDFIKKTLDVKSIHFDSAWVPYTNFSPIYQGKCGMSGDRVEGKIIY
ESCHERICHIA_MULTISPECIES_CADA                 AVITNSTYDGLLYNTDFIKKTLDVKSIHFDSAWVPYTNFSPIYEGKCGMSGGRVEGKVIY
KLEBSIELLA_MULTISPECIES_WP_012968785          AVITNSTYDGLLYNTDFIKKTLDVKSIHFDSAWVPYTNFSPIYEGKCGMSGGRVEGKVIY
ENTEROBACTERIAECEAE_MULTISPECIES_WP_002892486.1 AVITNSTYDGLLYNTDFIKKTLDVKSIHFDSAWVPYTNFSPIYEGKCGMSGGRVEGKVIY
                                              ******************************************:.******:*****:**

SALMONELLA_ENTERICA_WP_001540636.1            ETQSTHKLLAAFSQASMIHVKGDINEETFNEAYMMHTTTSPHYGIVASTETAAAMMKGNA
ESCHERICHIA_MULTISPECIES_CADA                 ETQSTHKLLAAFSQASMIHVKGDVNEETFNEAYMMHTTTSPHYGIVASTETAAAMMKGNA
KLEBSIELLA_MULTISPECIES_WP_012968785          ETQSTHKLLAAFSQASMIHVKGDVNEETFNEAYMMHTTTSPHYGIVASTETAAAMMKGNA
ENTEROBACTERIAECEAE_MULTISPECIES_WP_002892486.1 ETQSTHKLLAAFSQASMIHVKGDVNEETFNEAYMMHTTTSPHYGIVASTETAAAMMKGNA
                                              ***********************:************************************
```

Figure 1-con't

```
SALMONELLA_ENTERICA_WP_001540636.1             GKRLINGSIERAIKFRKEIKRLKSESDGWFFDVWQPEHIDGAECWPLRSDSAWHGFKNID
ESCHERICHIA_MULTISPECIES_CADA                  GKRLINGSIERAIKFRKEIKRLRTESDGWFFDVWQPDHIDTTECWPLRSDSTWHGFKNID
KLEBSIELLA_MULTISPECIES_WP_012968785           GKRLIDGSIERSIKFRKEIKRLKGESDGWFFDVWQPEHIDGPECWPLRSDSAWHGFKNID
ENTEROBACTERIAECEAE_MULTISPECIES_WP_002892486.1 GKRLIDGSIERSIKFRKEIKRLKGESDGWFFDVWQPEHIDGPECWPLRSDSAWHGFKNID
                                               *****:************:*********:***  ********:*********

SALMONELLA_ENTERICA_WP_001540636.1             NEHMYLDPIKVTLILTPGMKKDGTMDEFGIPASLVAKYLDERGIIVEKTGPYNLLFLFSIG
ESCHERICHIA_MULTISPECIES_CADA                  NEHMYLDPIKVTLLLTPGMEKDGTMSDFGIPASIVAKYLDEHGIVVEKTGPYNLLFLFSIG
KLEBSIELLA_MULTISPECIES_WP_012968785           NEHMYLDPIKVTLLLTPGMKKDGTMDDFGIPASIVAKYLDEHGIVVEKTGPYNLLFLFSIG
ENTEROBACTERIAECEAE_MULTISPECIES_WP_002892486.1 NEHMYLDPIKVTLLLTPGMKKDGTMDDFGIPASIVAKYLDEHGIVVEKTGPYNLLFLFSIG
                                               ************:******:****.****:*******:**:**************

SALMONELLA_ENTERICA_WP_001540636.1             IDKTKALSLLRALTEFKRAFDLNLRVKNILPALYREAPEFYENMRIQELAQNIHKLVEHH
ESCHERICHIA_MULTISPECIES_CADA                  IDKTKALSLLRALTDFKRAFDLNLRVKNMLPSLYREDPEFYENMRIQELAQNIHKLIVHH
KLEBSIELLA_MULTISPECIES_WP_012968785           IDKTKALSLLRALTDFKRAFDLNLRVKNMLPSLYREDPEFYENMRIQDLAQNIHKLIEHH
ENTEROBACTERIAECEAE_MULTISPECIES_WP_002892486.1 IDKTKALSLLRALTDFKRAFDLNLRVKNMLPSLYREDPEFYENMRIQDLAQNIHKLIEHH
                                               *************:*************:**:****.********: *******:  **

SALMONELLA_ENTERICA_WP_001540636.1             NLPDLMYRAFEVLPKMVMTPYTAFQKELHGETEEVYLEEMVGRVNANMILPYPPGVPLVM
ESCHERICHIA_MULTISPECIES_CADA                  NLPDLMYRAFEVLPTMVMTPYAAFQKELHGMTEEVYLDEMVGRINANMILPYPPGVPLVM
KLEBSIELLA_MULTISPECIES_WP_012968785           NLPDLMFRAFEVLPSMVMTPYAAFQKELHGQTEEVYLEEMVGRVNANMILPYPPGVPLVM
ENTEROBACTERIAECEAE_MULTISPECIES_WP_002892486.1 NLPDLMFRAFEVLPSMVMTPYAAFQKELHGQTEEVYLEEMVGRVNANMILPYPPGVPLVM
                                               ******:*******:******:*******  ******:*****:****************

SALMONELLA_ENTERICA_WP_001540636.1             PGEMITEESRPVLEFLQMLCEIGAHYPGFETDIHGAYRQADGRYTVKVLKENTK--
ESCHERICHIA_MULTISPECIES_CADA                  PGEMITEESRPVLEFLQMLCEIGAHYPGFETDIHGAYRQADGRYTVKVLKEESKK*
KLEBSIELLA_MULTISPECIES_WP_012968785           PGEMITEESRPVLEFLQMLCEIGAHYPGFETDIHGAYRQADGRYTVKVLKEENNK-
ENTEROBACTERIAECEAE_MULTISPECIES_WP_002892486.1 PGEMITEESRPVLEFLQMLCEIGAHYPGFETDIHGAYRQADGRYTVKVLKEENNK-
                                               ****************************************************:.:
```

LYSINE DECARBOXYLASES HAVING MODIFICATIONS AT TITRATABLE AMINO ACIDS

CROSS REFERENCE TO RELATED APPLICATION

This application is a 35 U.S.C. § 371 National Stage of International Application No. PCT/CN2016/113516, filed 30 Dec. 2016, designating the United States. Each application is incorporated herein by reference in its entirety.

BACKGROUND OF THE INVENTION

Most enzymes function optimally within a narrow pH range, because they are amphoteric molecules. The pH of the surrounding environment directly affects the charges on the acidic and basic groups of the amino acids that make up the enzyme. These changes in charge affect the net charge of the enzyme, the pKa of the active site, and the charge distribution across the surface of the enzyme. As a result, changes in pH can affect the activity, solubility, and stability of an enzyme.

The class of proteins known as acid decarboxylases is a group of enzymes that catalyze the decarboxylase reaction of basic amino acids (e.g., lysine, arginine, ornithine) in order to generate polyamines as part of the acid stress response in many microorganisms Escherichia coli has several PLP-dependent acid decarboxylases: CadA, LdcC, AdiA, SpeA, SpeC, SpeF, GadA, and GadB. All of these enzymes function within a narrow pH range, and the enzyme activity decreases significantly outside of that pH range (Kanjee et al., Biochemistry 50, 9388-9398, 2011). It has been previously observed that these PLP-dependent decarboxylases dimerize in order to form a complete active site. In some cases, such as CadA, the dimers form decamers that aggregate into higher molecular weight protein complexes required for optimal function. The inhibition of higher molecular weight protein complex formation (e.g., in conditions outside of the optimal pH) leads to a significant decrease in function (Kanjee et al., The EMBO Journal 30, 931-944, 2011).

The pKa values of individual amino acids in a protein are important for determining its biomolecular function, because one of the dominant reactions in a protein-water solution is the exchange of protons by certain amino acids with the environment of the protein. The pKa is a measure of the difference in free energy between neutral and charged states, and indicates the propensity of an amino acid to donate or accept a proton. Certain amino acids have titratable groups that make them more amenable to accept and donate protons. These amino acids include aspartate, glutamate, cysteine, serine, tyrosine, threonine, histidine, lysine, and arginine. Sample pKa values of some amino acids are: aspartate is 4.0, glutamate is 4.4, cysteine is 8.7, tyrosine is 9.6, histidine is 6.3, lysine is 10.4, and arginine is 13.0 (Nielsen J E & Vriend G, Proteins 43, 403-412, 2001). These pKa values can vary by 0.5 depending on the literature source.

Whether a titratable group accepts or donates a proton will depend on its environment, such as the pH or other amino acids in its proximity. For example, when the pH is less than the pKa of the titratable group, then the group will more likely accept a proton. Conversely, when the pH is greater than the pKa of the titratable group, then the group will more likely donate a proton. When a titratable group of an amino acid either accepts or donates a proton, the amino acid can become either positively charged, negatively charged, or neutral depending on the charge it started with before the proton exchange happened. Charged groups can interact with other charged groups when the two groups are brought into proximity of one another. Like charges repel each other and opposite charges attract each other. Neutrally charged groups that are protonated can still interact with other groups through hydrogen bond interactions.

An understanding of the pKa values of the titratable groups of a protein is not only important for understanding how pH affects polypeptide folding and enzyme activity, but also protein-protein interactions (Jensen J E, Curr Pharm Biotechnol 9, 96-102, 2008), especially in the cases of the acid decarboxylases that undergo significant changes in their quaternary structure as a result of a change in the pH of the environment. Tolerance to alkaline pH by acid decarboxylases is important, because the polyamines they generate as a product increase the pH of the reaction environment. Therefore, the activity of the acid decarboxylase usually decreases as more polyamines are generated, which can cause the decarboxylation reaction to stop prematurely when the pH of the reaction environment surpasses the pH range tolerated by the wild-type acid decarboxylase. There have been few studies evaluating the effect of mutations at various amino acids with titratable groups on the function of the acid decarboxylases.

Based on prior literature (Kanjee, et al. The EMBO Journal 30, 931-944, 2011), CadA transitions from a state that consists of decamers and high-order oligomers to a state that is composed mostly of dimers when the pH of the environment changes. The formation of decamers is a prerequisite for the formation of high-order oligomers. It has been shown that CadA functions optimally at a pH of 5.0-5.5 (Lemonnier M & Lane D, Microbiology 144, 751-760, 1998). At this acidic pH, Kanjee et al. show using EM that CadA exists mainly as high-order oligomers. When the pH is increased above 6.0 or when the inhibitor ppGpp is present, the high-order oligomers do not form and decarboxylase function is significantly reduced. However, there is an absence of literature that describes how the CadA high-order oligomers form and the amino acid residues that play a role in their formation.

BRIEF SUMMARY OF ASPECTS OF THE DISCLOSURE

This invention is based, in part, on the discovery of mutations that provide the ability to stabilize the chemical interaction necessary for quaternary structure formation, and increased stability to allow a mutant protein to function across a wider pH range. The ability to function across a wider pH range is important in maintaining a high reaction rate without the need to add additional chemicals to maintain pH. The maintenance of a high reaction rate across a wide pH range would enable lysine to be converted into cadaverine faster and reduce the amount of utilities required. The tolerance of the protein for alkaline pH eliminates the need to add additional chemicals to maintain pH. These chemicals used to maintain pH often times form salts e.g., ($SO_4^{2-}$ or $Cl^-$) that go either into the wastewater or must be removed from the process using additional purification steps. Therefore, a mutant acid decarboxylase that functions at a wider pH range than wild-type would decrease the cost and the environmental footprint of the overall process by reducing the amount of salts formed during the process.

The amino acid histidine has a pKa of 6.3, which is the pH at which the acid decarboxylase protein CadA transitions between different oligomeric states. A change in oligomeric state also changes the activity of the protein. At least one histidine residue in the CadA protein appears to play an important role in detecting the pH of the environment. The link between pH and CadA function is consistent with the function of the CadA protein as part of the acid stress response system. When the pH of the environment is sufficiently high, there is no need for the CadA protein to continue to synthesize polyamines that would further increase the pH of the environment. When the pH of the environment drops below the pKa of a histidine residue, the histidine residue can undergo a change in the protonation state of the titratable group causing the CadA protein to transition from a higher to lower oligomeric state and thus affect the activity of the CadA protein.

There are a total of 24 histidine residues in the CadA protein from *Escherichia coli* (SEQ ID NO: 2), of which 2 are located at the N-terminal wing domain (H9 and H23), 1 is located in the linker region (H152), 11 are located in the PLP-binding subdomain (H193, H197, H245, H250, H282, H300, H328, H366, H379, H396, H402), 4 are located in subdomain 4 (H458, H474, H483, H521), and 6 are located in the C-terminal domain (H594, H599, H600, H629, H685, H694). A sequence alignment of the CadA protein sequence from *Escherichia* with that from *Klebsiella*, Enterobacteriaceae, and *Salmonella enterica* indicate that all 24 histidine residues except for one (H521) are conserved (FIG. 1). The CadA equivalent protein from *Salmonella enterica* has an arginine residue at amino acid position 521.

In one aspect, the invention thus provides a CadA variant polypeptide comprising at least one amino acid substitution in a region corresponding to amino acids 455 to 483 as determined with reference to SEQ ID NO: 2, wherein the at least one amino acid substitution is selected from positions 457 and/or 458; and wherein the CadA variant polypeptide has at least 70% identity to any one of SEQ ID NOS:2 to 5. In some embodiments, the CadA variant polypeptide comprises substitutions at positions 457 and 458. In some embodiments, the amino acid substitution is H458A/C/E/F/G/M/P/T/V/W/Y, or D457A/C/E/F/H/I/K/L/M/N/S/W/Y. In some embodiments, the amino acid substitution is H458A/C/F/M/V/W/Y, or D457A/C/H/K/L/M/N/S. In some embodiments, the CadA variant polypeptide further comprises an aspartate substitution at position 460 as determined with reference to SEQ ID NO: 2. In some embodiments, the aspartate substitution is D460C/F/Q/I/S/V/W/Y, D460C/F/Q/I/S/V/W, or D460F/V/W/Y. In some embodiments, a CadA variant polypeptide as described above in this paragraph has at least 70% identity to SEQ ID NO:2. In some embodiments, the CadA variant polypeptide has at least 75%, at least 80%, at least 85%, at least 90%, or at least 95% identity to SEQ ID NO:2. In some embodiments, a CadA variant polypeptide has at least 70% identity to SEQ ID NO:3, SEQ ID NO:4, or SEQ ID NO:5. In some embodiments, the CadA variant polypeptide has at least 75%, at least 80%, at least 85%, at least 90%, or at least 95% identity to SEQ ID NO:3, SEQ ID NO:4, or SEQ ID NO:5. In some embodiments, the CadA variant comprises the amino acid sequence of SEQ ID NO:3, SEQ ID NO:4, or SEQ ID NO:5 in which aspartate at position 457 is substituted, e.g., a substitution D457A/C/E/F/H/I/K/L/M/N/S/W/Y or a substitution D457A/C/H/K/L/M/N/S; histidine at position 458 is substituted, e.g., a substitution H458A/C/E/F/G/M/P/T/V/W/Y or H458A/C/F/M/V/W/Y; or asparate at position 460 is substituted, e.g., a substitution D460C/F/Q/I/S/V/W or D460F/V/W/Y. In some embodiments, the CadA variant comprises the amino acid sequence of SEQ ID NO:3, SEQ ID NO:4, or SEQ ID NO:5 in which one of the amino acids at positions D457, H458, and D460 is substituted; or two of the amino acids at positions D457, H458, and D460 are substituted. In some embodiments, the CadA variant comprises the amino acid sequence of SEQ ID NO:3, SEQ ID NO:4, or SEQ ID NO:5 in which all of positions D457, H458, and D460 are substituted.

In a further aspect, the invention provides a genetically modified host cell comprising a CadA variant polypeptide as described herein, e.g., in the preceding paragraph. In typical embodiments, the genetically modified host cell is genetically modified to over express one or more lysine biosynthesis polypeptides. In some embodiments, the host cell is a bacterium. In further embodiments, the host cell is from the genus *Escherichia*, e.g., *Escherichia coli*; or *Hafnia*, e.g., *Hafnia alvei*, or *Corynebacterium* e.g., *Corynebacterium glutamicum*.

In an additional aspect, the invention provides a polynucleotide comprising a nucleic acid sequence encoding a CadA variant polypeptide as described herein, e.g., in the preceding paragraphs in this section. In some embodiments, a CadA variant polypeptide as described in the preceding paragraph of this section has at least 70% identity to SEQ ID NO:2. In some embodiments, the CadA variant polypeptide has at least 75%, at least 80%, at least 85%, at least 90%, or at least 95% identity to SEQ ID NO:2. In some embodiments, a CadA variant polypeptide has at least 70% identity to SEQ ID NO:3, SEQ ID NO:4, or SEQ ID NO:5. In some embodiments, the CadA variant polypeptide has at least 75%, at least 80%, at least 85%, at least 90%, or at least 95% identity to SEQ ID NO:3, SEQ ID NO:4, or SEQ ID NO:5. In further aspects, the invention additionally provides an expression vector comprising a polynucleotide encoding the CadA variant and/or a genetically modified host cell comprising the expression vector. In some embodiments, the host cell is a bacterium, e.g., from the genus *Escherichia* or *Hafnia*. In some embodiments, the host cell is from the genus *Corynebacterium* e.g., *Corynebacterium glutamicum*. In some embodiments, the genetically modified host cell is *Escherichia coli*. In some embodiments, the genetically modified host cell is *Hafnia alvei*. In some embodiments, the genetically modified host cell is *Corynebacterium glutamicum*.

In a further aspect, the invention provides a genetically modified host cell comprising a polynucleotide that comprises a nucleic acid sequence encoding a CadA variant polypeptide as described herein, e.g., in the preceding paragraphs in this section, wherein the nucleic acid sequence encoding the CadA variant polypeptide is integrated into the host cell chromosome. In some embodiments, the host cell is a bacterium, e.g., from the genus *Escherichia*, *Corynebacterium* or *Hafnia*. In some embodiments, the genetically modified host cell is *Escherichia coli*. In some embodiments, the genetically modified host cell is *Hafnia alvei*. In some embodiments, the genetically modified host cell is *Corynebacterium glutamicum*.

In another aspect, the invention provides a method of producing cadaverine, the method comprising culturing a genetically modified host cell as described herein, e.g., in the preceding paragraphs in this section, under conditions in which CadA variant polypeptide is expressed.

In one aspect, the invention thus provides a genetically modified host cell comprising a CadA variant polypeptide having at least one amino acid substitution in a region corresponding to amino acids 455 to 483 as determined with reference to SEQ ID NO: 2, wherein the at least one amino acid substitution is selected from the group consisting of positions 457, 458, and 460; wherein the CadA variant polypeptide has at least 70% identity to any one of SEQ ID NOS:2 to 5; and wherein the host cell is from the genus *Hafnia, Escherichia,* or *Corynebacterium*. In typical embodiments, the genetically modified host cell is genetically modified to over express one or more lysine biosynthesis polypeptides. In some embodiments, the host cell is *Hafnia alvei*. In some embodiments, the host cell is *Escherichia coli*. In some embodiments, the host cell is *Corynebacterium glutamicum*. In some embodiments, the CadA variant polypeptide comprises an amino acid substitution at position 457. In some embodiments, the amino acid substitution is D457A/C/E/F/H/I/K/L/M/N/S/W/Y. In some embodiments, the amino acid substitution is D457A/C/H/K/L/M/N/S. In some embodiments, the CadA variant polypeptide comprises an amino acid substitution at position 458. In some embodiments, the amino acid substitution is H458A/C/E/F/G/M/P/T/V/W/Y. In some embodiments, the amino acid substitution is H458A/C/F/M/V/W/Y. In some embodiments, the CadA variant polypeptide comprises an amino acid substitution at position 460. In some embodiments, the amino acid substitution is D460C/F/Q/I/S/V/W/Y. In some embodiments, the amino acid substitution is D460C/F/Q/I/S/V/W. In some embodiments, the amino acid substitution is D460F/V/W/Y. In some embodiments, the CadA variant polypeptide has at least two amino acid substitutions selected from the group of positions consisting of 457, 458, and 460. In some embodiments, the CadA variant polypeptide has at least three amino acid substitutions selected from the group of positions consisting of 457, 458, and 460. In some embodiments, the CadA variant polypeptide has amino acid substitutions 457, and 458. In some embodiments, the CadA variant polypeptide has amino acid substitutions 458, and 460. In some embodiments, the CadA variant polypeptide has amino acid substitutions 457, and 460. In some embodiments, a CadA variant polypeptide as described above in this paragraph has at least 70% identity to SEQ ID NO:2. In some embodiments, the CadA variant polypeptide has at least 75%, at least 80%, at least 85%, at least 90%, or at least 95% identity to SEQ ID NO:2. In some embodiments, a CadA variant polypeptide has at least 75%, at least 80%, at least 85%, at least 90%, or at least 95% identity to SEQ ID NO:3, SEQ ID NO:4, or SEQ ID NO:5.

In an additional aspect, the invention provides a polynucleotide comprising a nucleic acid sequence encoding a CadA variant polypeptide as described herein, e.g., in the preceding paragraph in this section. In some embodiments, a CadA variant polypeptide as described in the preceding paragraph of this section has at least 70% identity to SEQ ID NO:2. In some embodiments, the CadA variant polypeptide has at least 75%, at least 80%, at least 85%, at least 90%, or at least 95% identity to SEQ ID NO:2. In some embodiments, a CadA variant polypeptide has at least 70% identity to SEQ ID NO:3, SEQ ID NO:4, or SEQ ID NO:5. In some embodiments, the CadA variant polypeptide has at least 75%, at least 80%, at least 85%, at least 90%, or at least 95% identity to SEQ ID NO:3, SEQ ID NO:4, or SEQ ID NO:5. In further aspects, the invention additionally provides an expression vector comprising a polynucleotide encoding the CadA variant and/or a genetically modified host cell comprising the expression vector. In some embodiments, the host cell is *Hafnia alvei*. In some embodiments, the host cell is *Escherichia coli*. In some embodiments, the host cell is *Corynebacterium glutamicum*.

In a further aspect, the invention provides a genetically modified host cell comprising a polynucleotide that comprises a nucleic acid sequence encoding a CadA variant polypeptide having at least one amino acid substitution in a region corresponding to amino acids 455 to 483 as determined with reference to SEQ ID NO: 2, wherein at least one amino acid substitution is selected from the group consisting of positions 457, 458, and 460; wherein the CadA variant polypeptide has at least 70% identity to any one of SEQ ID NOS:2 to 5; wherein the host cell is from the genus *Hafnia, Escherichia,* or *Corynebacterium*, and wherein the nucleic acid sequence encoding the CadA variant polypeptide is integrated into the host cell chromosome. In some embodiments, the host cell is from the genus *Hafnia, Escherichia,* or *Corynebacterium*. In some embodiments, the genetically modified host cell is *Hafnia alvei*. In some embodiments, the host cell is *Escherichia coli*. In some embodiments, the host cell is *Corynebacterium glutamicum*.

In another aspect, the invention provides a method of producing cadaverine, the method comprising culturing a genetically modified host cell as described herein, e.g., in the preceding paragraph in this section, under conditions in which CadA variant polypeptide is expressed.

DESCRIPTION OF THE FIGURES

FIG. 1 shows an alignment of the *E. coli* CadA polypeptide sequence SEQ ID NO:2 with CadA homologs from *Salmonella enterica* (WP 001540636.1, SEQ ID NO:5), *Klebsiella* multispecies (WP 012968785. SEQ ID NO:3), and Enterobacteriaeceae multispecies (WP 002892486.1, SEQ ID NO:4).

DETAILED DESCRIPTION OF ASPECTS OF THE DISCLOSURE

Before the present invention is described, it is to be understood that this invention is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications and accession numbers mentioned herein are incorporated herein by reference to disclose and describe the methods and/or materials in connection with which the publications are cited.

Terminology

As used in the context of the present disclosure, a "CadA polypeptide" refers to an *Escherichia coli* CadA polypeptide having the amino acid sequence of SEQ ID NO:2, or a biologically active variant thereof that has activity, i.e., catalyzes the decarboxylation of L-lysine to produce cadaverine. Biologically active variants include alleles, mutants, fragments, and interspecies homologs of the *E. coli* CadA polypeptide. CadA has been well characterized structurally and functionally. The protein data bank ID for the structure of CadA is 3N75. Illustrative CadA polypeptides from other species include CadA from *Klebsiella* (e.g., SEQ ID NO:3), Enterobacteriaceae (e.g., SEQ ID NO:5), and *Salmonella enterica* (e.g., SEQ ID NO:6). Additional CadA polypeptides from other species include *Serratia* sp., WP 033635725.1; and *Raoultella ornithinolytica*, YP 007874766.1. In some embodiments, a "CadA polypeptide" has at least 60% amino acid sequence identity, typically at least 65%, 70%, 75%, 80%, 85%, 90% identity; often at least 91%, 92%, 93%, 94%, 95%, 96%, 97%, 98% or 99% or greater amino acid sequence identity, over a region of at least about 200, 300, 400, 500, or more, amino acids; or over the length of the CadA polypeptide of SEQ ID NO:2. In some embodiments, a "CadA polypeptide" comprises a region that has at least 80%, at least 85%, at least 90%, at least 95%, or at least 91%, 92%, 93%, 94%, 95%, 96%, 97%, 98% or 99% or greater amino acid sequence identity over a region comprising amino acids residues that correspond to amino acids 455 to 483 of SEQ ID NO:2 where a native histidine or aspartate present in the region is substituted with another non-naturally occurring amino acid as described herein. In some embodiments, a "CadA polypeptide" has at least 60% amino acid sequence identity, often at least 65%, 70%, 75%, 80%, 85%, 90%, 91%, 92%, 93%, 94%, 95%, 96%, 97%, 98% or 99% or greater, amino acid sequence identity, preferably over a region of at least about 200, 300, 400, 500, or more, amino acids, or over the length of the CadA polypeptide of SEQ ID NO:3, SEQ ID NO:4, or SEQ ID NO:5.

A "CadA polynucleotide" as used herein refers to a polynucleotide that encodes a CadA polypeptide. A nucleic acid or polynucleotide that encodes a CadA refers to a gene, pre-mRNA, mRNA, and the like, including nucleic acids encoding variants, alleles, fragments, mutants, and interspecies homologs of the particular amino acid sequences described herein.

As used herein, the term "alkaline pH" refers to a solution or surrounding environment having a pH of greater than 7.5. In one embodiment, alkaline pH refers to a solution or surrounding environment have a pH of at least 8.0, at least 8.5, or higher.

The term "enhanced" or "improved" in the context of the production of an amino acid derivative, e.g., cadaverine, as used herein refers to an increase in the production of the amino acid derivative produced by a host cell that expresses a CadA variant polypeptide of the invention in comparison to a control counterpart cell, such as a cell of the wildtype strain or a cell of the same strain that expresses the wildtype CadA protein. In one embodiment, activity of the CadA variant is improved by at least 10%, 15% 20%, 30%, 40%, 50%, 60%, 70%, 80%, 90%, 100%, or greater, compared to CadA activity of a counterpart cell expressing a wildtype CadA, where activity is assessed by measuring the production of an amino acid derivative, typically cadaverine, produced by the host cell and control cell under identical conditions. For example, activity of a CadA variant polypeptide of the invention can be assessed by evaluating an aliquot of a culture of host cells transformed with a polynucleotide encoding the variant CadA polypeptide compared to a corresponding aliquot from a culture of counterpart host cells of the same strain that expresses wildtype CadA. By way of further illustration, the activity of a CadA variant polypeptide of the invention compared to the counterpart wildtype CadA can be determined by evaluating the production of cadaverine by cells transformed with either a vector comprising a nucleic acid sequence encoding the variant CadA polypeptide (variant host cells) or a vector comprising a nucleic acid encoding the wildtype CadA polypeptide (control host cells). Variant and control host cells that are grown under conditions to express CadA and an aliquot is incubated with lysine-HCl and PLP at a final concentration of 120 g/L and 0.1 mM, respectively at pH 8.0 for a period of time, e.g., 2 hours. Cadaverine production is measured following incubation. An exemplary assay is provided in the Examples section.

The terms "numbered with reference to", or "corresponding to," or "determined with reference to" when used in the context of the numbering of a given amino acid or polynucleotide sequence, refers to the numbering of the residues of a specified reference sequence when the given amino acid or polynucleotide sequence is compared to the reference sequence. For example, a position of a variant CadA polypeptide sequence "corresponds to" a position in SEQ ID NO:2 when the variant polypeptide is aligned with SEQ ID NO:2 in a maximal alignment.

The terms "wild type", "native", and "naturally occurring" with respect to a CadA polypeptide are used herein to refer to a CadA protein that has a sequence that occurs in nature.

In the context of this invention, the term "mutant" with respect to a mutant polypeptide or mutant polynucleotide is used interchangeably with "variant". A "non-naturally" occurring CadA variant refers to a variant or mutant CadA polypeptide that is not present in a cell in nature and that is produced by genetic modification, e.g., using genetic engineering technology or mutagenesis techniques, of a native CadA polynucleotide or polypeptide. A "variant" CadA polypeptide in the context of this disclosure includes any CadA polypeptide that comprises at least one amino acid substitution, where the at least one amino acid substitution is a substitution of a histidine or aspartate residue at positions 457, 458, and 460, as determined with reference to SEQ ID NO:2. A variant CadA polypeptide of the invention may also have additional mutations relative to SEQ ID NO:2, including further substitutions, insertions, or deletions.

The terms "polynucleotide" and "nucleic acid" are used interchangeably and refer to a single or double-stranded polymer of deoxyribonucleotide or ribonucleotide bases read from the 5' to the 3' end. A nucleic acid as used in the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of this disclosure for two nucleic acids or polypeptides, refers to a sequence that has at least 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

An algorithm that may be used to determine whether a variant CadA polypeptide has sequence identity to SEQ ID NO:2, or another polypeptide reference sequence such as SEQ ID NO:3, SEQ ID NO:4, or SEQ ID NO:5, is the BLAST algorithm, which is described in Altschul et al., 1990, J. Mol. Biol. 215:403-410). Software for performing BLAST analyses is publicly available through the National Center for Biotechnology Information (on the worldwide web at ncbi.nlm.nih.gov/). Illustrative software for performing protein sequence alignments include ClustalW2 and BLASTP. For amino acid sequences, the BLASTP program uses as defaults a word size (W) of 3, an expect threshold (E) of 10, and the BLOSUM62 scoring matrix (see Henikoff & Henikoff, Proc. Natl. Acad. Sci. USA 89:10915 (1989)). In the present disclosure, polypeptide sequence identity is typically determined using BLASTP Align Sequence with the default parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and FASTA in the Wisconsin Genetics Software Package, Genetics Computer Group, 575 Science Dr., Madison, Wis.), or by manual alignment and visual inspection. Optimal alignments are typically conducted using BLASTP with default parameters.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

The term "polypeptide" as used herein includes reference to polypeptides containing naturally occurring amino acids and amino acid backbones as well as non-naturally occurring amino acids and amino acid analogs.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T) and Cys (Cysteine or C). Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His and Trp; and the "phenyl sub-group" comprising Phe and Tyr. In another further example, the aliphatic group can be sub-divided into sub-groups including: the "large aliphatic non-polar sub-group" comprising Val, Leu and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained;

Glu for Asp or vice versa, such that a negative charge can be maintained; Ser for Thr or vice versa, such that a free—OH can be maintained; and Gln for Asn or vice versa, such that a free—NH2 can be maintained. The following six groups each contain amino acids that further provide illustrative conservative substitutions for one another. 1) Ala, Ser, Thr; 2) Asp, Glu; 3) Asn, Gln; 4) Arg, Lys; 5) Ile, Leu, Met, Val; and 6) Phe, Try, and Trp (see, e.g., Creighton, Proteins (1984)). In some embodiments, conservative substitutions are employed in generating CadA variants having substitutions at sites other than a histidine or aspartate residue.

As used in the context of the present disclosure, a "titratable group" refers to an amino acid side chain capable of donating or accepting a proton as a result of a change in pH. In one embodiment, a titratable group can be found at various amino acids along the CadA protein. In one embodiment, amino acids having a titratable group include aspartate, glutamate, cysteine, serine, tyrosine, threonine, histidine, lysine, and arginine. While not wishing to be bound by the following, it is believed a titratable group allows for rotation or orientation of the amino acid side chain such that a neighboring amino acid pKa (i.e., an amino acid within 4 angstroms of the titratable group) can be influenced by the titratable group. In one embodiment, a distance of less than 2 angstroms between the titratable group of one amino acid and a neighboring amino acid is considered a strong interaction. In another embodiment, a distance of more than 4 angstroms between the titratable group of one amino acid with a neighboring amino acid is considered a weak interaction.

For the purpose of this invention, a "triad of amino acids" refers to an occurrence of a histidine and two neighboring acidic amino acids having a titratable group where the histidine has a pKa value that is close to the pH at which CadA transitions between different oligomeric states as determined using the linearized Poisson-Boltzmann equation-based pKa calculation method to predict the pKa values of the histidine residues in the CadA protein. In one embodiment, a triad of amino acids comprises at least one substitution of an aspartic acid residue at position 457, a histidine residue at position 458, and an aspartic acid residues as position 460, as determined with reference to SEQ ID NO:2. In another embodiment, a triad of amino acids comprises at least two substitutions, wherein the at least two substitutions are selected from an aspartic acid residue at position 457, a histidine residue at position 458, and an aspartic acid residues as position 460, as determined with reference to SEQ ID NO:2. In another embodiment, a triad of amino acids comprises substitutions at each of the three residues aspartic acid residue at position 457, histidine residue at position 458, and aspartic acid residues as position 460, as determined with reference to SEQ ID NO:2.

The term "promoter," as used herein, refers to a polynucleotide sequence capable of driving transcription of a nucleic acid sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a repressor binding sequence and the like. These cis-acting sequences typically interact with proteins or other biomolecules to carry out (turn on/off, regulate, modulate, etc.) gene transcription. Most often the core promoter sequences lie within 1-2 kb of the translation start site, more often within 1 kbp and often within 500 bp or 200 bp or fewer, of the translation start site. By convention, promoter sequences are usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wild type, native promoter as well as variants of the promoter that retain the ability to induce expression. Reference to a promoter by name is not restricted to a particular species, but also encompasses a promoter from a corresponding gene in other species.

A "constitutive promoter" in the context of this invention refers to a promoter that is capable of initiating transcription under most conditions in a cell, e.g., in the absence of an inducing molecule. An "inducible promoter" initiates transcription in the presence of an inducer molecule.

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different species). Similarly, a polypeptide is "heterologous" to a host cell if the native wildtype host cell does not produce the polypeptide.

The term "exogenous" refers generally to a polynucleotide sequence or polypeptide that does not naturally occur in a wild-type cell or organism, but is typically introduced into the cell by molecular biological techniques, i.e., engineering to produce a recombinant microorganism. Examples of "exogenous" polynucleotides include vectors, plasmids, and/or man-made nucleic acid constructs encoding a desired protein or enzyme.

The term "endogenous" refers to naturally-occurring polynucleotide sequences or polypeptides that may be found in a given wild-type cell or organism. In this regard, it is also noted that even though an organism may comprise an endogenous copy of a given polynucleotide sequence or gene, the introduction of a plasmid or vector encoding that sequence, such as to over-express or otherwise regulate the expression of the encoded protein, represents an "exogenous" copy of that gene or polynucleotide sequence. Any of the pathways, genes, or enzymes described herein may utilize or rely on an "endogenous" sequence, which may be provided as one or more "exogenous" polynucleotide sequences, or both.

"Recombinant nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence can have two or more sequences from unrelated genes arranged to make a new functional nucleic acid.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a polypeptide of the invention protein operably linked to a promoter, e.g., its native promoter, where the expression cassette is introduced into a heterologous microorganism. In some embodiments, an expression cassette comprises a polynucleotide sequence encoding a polypeptide of the invention where the polynucleotide is targeted to a position in the genome of a microorganism such that expression of the polynucleotide sequence is driven by a promoter that is present in the microorganism.

The term "host cell" as used in the context of this invention refers to a microorganism and includes an individual cell or cell culture that can be or has been a recipient of any recombinant vector(s) or isolated polynucleotide(s) of the invention. Host cells include progeny of a single host cell, and the progeny may not necessarily be completely identical (in morphology or in total DNA complement) to the original parent cell due to natural, accidental, or deliberate mutation and/or change. A host cell includes cells into which a recombinant vector or a polynucleotide of the invention has been introduced, including by transformation, transfection, and the like. In some embodiments, the host cell is from the genus *Escherichia, Corynebacterium* or *Hafnia*.

The term "isolated" refers to a material that is substantially or essentially free from components that normally accompany it in its native state. For example, an "isolated polynucleotide," as used herein, may refer to a polynucleotide that has been isolated from the sequences that flank it in its naturally-occurring or genomic state, e.g., a DNA fragment that has been removed from the sequences that are normally adjacent to the fragment, such as by cloning into a vector. A polynucleotide is considered to be isolated if, for example, it is cloned into a vector that is not a part of the natural environment, or if it is artificially introduced in the genome of a cell in a manner that differs from its naturally-occurring state. Alternatively, an "isolated peptide" or an "isolated polypeptide" and the like, as used herein, refers to a polypeptide molecule that is free of other components of the cell, i.e., it is not associated with in vivo cellular components.

The invention employs various routine recombinant nucleic acid techniques. Generally, the nomenclature and the laboratory procedures in recombinant DNA technology described below are commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009-2016).

Summary of Certain Aspects of the Disclosure

In one aspect, the invention provides a variant CadA polypeptide that comprises a mutation at a histidine and/or an aspartic acid (aspartate) residue in a region corresponding to amino acids 455 to 483 as determined by reference to SEQ ID NO:2. In one embodiment, the mutation includes substitution of a histidine residue at position 458 with reference to SEQ ID NO:2 located within a flexible loop of the CadA protein. In another embodiment, mutation of a histidine and/or an aspartic acid residue comprises one or more amino acids having a titratable group. In one embodiment, the CadA variant polypeptide comprises an amino acid substitution in a region corresponding to amino acids 455 to 483 as determined with reference to SEQ ID NO: 2, wherein the amino acid substitution comprises a triad of amino acids having a titratable group. In one embodiment, the triad of amino acids comprises substitution of amino acid residues at positions 457, 458, and 460, with reference to SEQ ID NO:2. In one embodiment, the mutation at a histidine or aspartic acid residue in the region corresponding to amino acids 455 and 483 as determined by reference to SEQ ID NO:2 comprises an amino acid amenable to protonation.

The ability of a variant CadA of the present invention to tolerate alkaline pH also allows the use of alternative nitrogen sources that have higher pH values, such as urea and ammonia (1M solution has a pH 11.6) in fermentation reactions to generate the desired product, e.g., polyamines. These alternative nitrogen sources generate less salt waste byproduct.

CadA Polypeptide Variants

CadA is a member of the subclass of Fold Type I pyridoxal 5'-phosphate (PLP)-dependent decarboxylases. This class of proteins typically contains a N-terminal wing domain, a core domain, and a C-terminal domain. The core domain is composed of a linker region, a PLP-binding subdomain, and subdomain 4 For CadA, the N-terminal wing domain (corresponding to residues 1 to 129 as determined with reference to SEQ ID NO:2) has a flavodoxin-like fold composed of five-stranded parallel beta-sheets sandwiched between two sets of amphipathic alpha-helices. The core domain (residues 130 to 563 as determined with reference to 563 of SEQ ID NO:2) includes: a linker region, amino acid residues 130 to 183 of SEQ ID NO:2, that form a short helical bundle; the PLP-binding subdomain, amino acids 184 to 417 of SEQ ID NO:2 that form a seven-stranded beta-sheet core surrounded by three sets of alpha-helices; and subdomain 4, amino acids 418 to 563 that form a four stranded antiparallel beta-sheet core with three alpha-helices facing outward. The C-terminal domain corresponds to amino acid residues 564 to 715 as determined with referenced to SEQ ID NO:2 that form two sets of beta sheets with an alpha-helical outer surface (Kanjee et al., The EMBO Journal 30, 931-944 2011).

CadA protein forms a two-fold symmetric dimer that completes the active site of each monomer. Five dimers associate to form a decamer that consist of a double-ringed structure with five-fold symmetry. The decamer associates with other decamers to form higher-order oligomers. It has been shown that in acidic conditions (pH 5), CadA predominantly exists in the oligomeric state, and less oligomers and decamers are found as the environment becomes more basic. It was estimated that 25% of the enzymes exist as dimers and 75% exist as decamers at pH 6.5, while 95% of the enzymes exist as dimers at pH 8.0 (Kanjee et al., The EMBO Journal 30, 931-944 2011). This decrease in oligomer formation coincides with the decrease in decarboxylase activity observed as the pH of the environment of the enzyme increases above 5.0.

Illustrative Cad A polypeptides from *E. coli, Salmonella enterica, Klebsiella*, and Enterobacteriaeceae are provided in SEQ ID NOS:2-5, which share greater than 90% sequence identity with one another.

There is research on various methods to calculate pKa values of a protein (Yang, et al., Proteins 15, 252-265, 1993; Van Vlijmen H W, et al., *Proteins* 33, 145-158, 1998; Rabenstein B & Knapp E W, *Biophysical Journal* 80, 1141-1150, 2001; Kieseritzky G & Knapp E W, *Proteins* 71, 1335-1348, 2008; Kilambi K P & Gray JJ, *Biophysical J* 103, 587-595, 2012). The difference between computational and experimental pKa values for most amino acid residues tested in the literature is 0.5-0.75. One method is the linearized Poisson-Boltzmann equation-based pKa calculation method to predict the pKa values of the 24 histidine residues in the CadA protein. A summary of the pKa values calculated herein is presented in Table 1. One histidine residue at position 458 with reference to SEQ ID NO:2 was found to have a pKa value close to the pH at which CadA transitions between different oligomeric states. According to the literature (Kanjee U, et al. *The EMBO Journal,* 30, 931-944, 2011), CadA transitions from a state consisting of decamers and high-order oligomers to a state consisting of mostly dimers when the pH of the environment changes. Therefore, a change in pH can affect those amino acids whose titratable groups have pKa values similar to the pH where the transition in oligomerization of the proteins takes place.

H458 is located on a flexible loop region of CadA that spans amino acids Q455 to H483. The flexibility of this loop allows neighboring amino acids (i.e., an amino acid within four angstroms of a titratable group) on adjacent secondary structures of the protein to interact with amino acids on the flexible loop as the loop moves in three-dimensional space. Therefore, it is possible for other acid or base groups in the vicinity to affect the pKa of H458 if movement of the flexible loop brings the neighboring amino acid within 4 Å of H458.

In one embodiment, CadA polypeptides of the present invention comprise at least one amino acid substitution in a region corresponding to amino acids 455 to 483 as determined with reference to SEQ ID NO: 2, wherein at least one amino acid substitution is selected from positions 457 and/or 458; and wherein the CadA variant polypeptide has at least 70% identity to any one of SEQ ID NOS:2 to 5. In one embodiment, the CadA variant comprises a substitution of a histidine residue at position 458. In some embodiments, the amino acid substitution is H458A/C/E/F/G/M/P/T/V/W/Y, or H458A/C/F/M/V/W/Y. In another embodiment, the CadA variant comprises a substitution of an aspartate residue at position 457. In one embodiment, the substitution is D457A/C/E/F/H/I/K/L/M/N/S/W/Y, or D457A/C/H/K/L/M/N/S. In some embodiments, the CadA variant polypeptide further comprises an aspartate substitution at position 460 as determined with reference to SEQ ID NO: 2. In some embodiments, the aspartate substitution is D460C/F/Q/I/S/V/W/Y, D460C/F/Q/I/S/V/W, or D460F/V/W/Y. In some embodiments, a CadA variant polypeptide as described above in this paragraph has at least 70% identity to SEQ ID NO:2. In some embodiments, the CadA variant polypeptide has at least 75%, at least 80%, at least 85%, at least 90%, or at least 95% identity to SEQ ID NO:2. In some embodiments, a CadA variant polypeptide has at least 70% identity to SEQ ID NO:3, SEQ ID NO:4, or SEQ ID NO:5. In some embodiments, the CadA variant polypeptide has at least 75%, at least 80%, at least 85%, at least 90%, or at least 95% identity to SEQ ID NO:3, SEQ ID NO:4, or SEQ ID NO:5.

In the present disclosure, the amino acid that is substituted for the histidine and/or aspartate residue does not occur at that position in a native CadA sequence. A variant CadA polypeptide in accordance with the invention thus can comprise at least one amino acid substitution at position D457 and/or H458 as determined with reference to SEQ ID NO:2. In some embodiments, the CadA variant can further comprise an amino acid substitution at position 460 as determined with reference to SEQ ID NO:2.

In another embodiment, CadaA variant polypeptides of the present invention comprise at least one amino acid substitution in a region corresponding to amino acids 455 to 483 as determined with reference to SEQ ID NO: 2, wherein the at least one amino acid substitution is selected from the group consisting of positions 457, 458, and 460; wherein the CadA variant polypeptide has at least 70% identity to any one of SEQ ID NOS:2 to 5; and wherein the host cell is from the genus *Hafnia*. In one embodiment, the CadA variant comprises a substitution of an aspartate residue at position 457. In one embodiment, the substitution is D457A/C/E/F/H/I/K/L/M/N/S/W/Y, or D457A/C/H/K/L/M/N/S. In one embodiment, the CadA variant comprises a substitution of a histidine residue at position 458. In some embodiments, the amino acid substitution is H458A/C/E/F/G/M/P/T/V/W/Y, or H458A/C/F/M/V/W/Y. In one embodiment, the CadA variant comprises an aspartate substitution at position 460 as determined with reference to SEQ ID NO: 2. In some embodiments, the aspartate substitution is D460C/F/Q/I/S/V/W/Y, D460C/F/Q/I/S/V/W, or D460F/V/W/Y. In some embodiments, the variant CadA polypeptide comprises more than one amino acid substitution, e.g., 2, 3, or more substitutions, at positions D457, H458, and D460 as determined with reference to SEQ ID NO:2. In one embodiment, the variant CadA polypeptide comprises an amino acid substitution at positions D457 and H458 as determined with reference to SEQ ID NO:2. In one embodiment, the variant CadA polypeptide comprises an amino acid substitution at positions D457 and D460 as determined with reference to SEQ ID NO:2. In one embodiment, the variant CadA polypeptide comprises an amino acid substitution at positions H458 and D460 as determined with reference to SEQ ID NO:2. In one embodiment, the variant CadA polypeptide comprises an amino acid substitution at positions D457, H458, and D460 as determined with reference to SEQ ID NO:2. In some embodiments, the CadA variant polypeptide has at least 75%, at least 80%, at least 85%, at least 90%, or at least 95% identity to SEQ ID NO:2. In some embodiments, a CadA variant polypeptide has at least 70% identity to SEQ ID NO:3, SEQ ID NO:4, or SEQ ID NO:5. In some embodiments, the CadA variant polypeptide has at least 75%, at least 80%, at least 85%, at least 90%, or at least 95% identity to SEQ ID NO:3, SEQ ID NO:4, or SEQ ID NO:5.

In one embodiment, a CadA polypeptide of the present invention comprises at least one amino acid substitution of a histidine and/or an aspartate residue in subdomain 4 of CadA (i.e., without a defined secondary structure (α, alpha helix; β, beta sheet; η strand) (see Kanjee et al.)); wherein rotation of the amino acid side chain (around the α carbon) brings the titratable group of D457 or D460 to within 4 angstroms of H458, thereby facilitating a strong interaction between a proton donor and a proton acceptor.

In some embodiments, a variant CadA polypeptide comprises more than one amino acid substitution, e.g., 2, 3, or more substitutions, at positions D457, H458 and D460 as determined with reference to SEQ ID NO:2. In some embodiments, the amino acid that is substituted for a histidine or aspartate is selected from the group of amino acids consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine, where the mutant does not have the same amino acid as the wild-type sequence (SEQ ID NOS:2, 3, 4, or 5) at the same position. In some embodiments, the amino acid that is substituted for a histidine or an aspartate has the ability to donate a hydrogen for hydrogen bond formation. For example, in general, amino acids C, Y, K, and R have pKa values greater than 8, so their protonation state does not change when the pH increases from 5 to 8. Therefore, any hydrogen bond formed at these positions is more stable compared to when aspartate, which has an acidic pKa, is present at that position. In some embodiments, the amino acid that is substituted for a histidine is selected from the group consisting of A, C, E, F, G, M, P, T, V, W, and Y. In some embodiments, the amino acid that is substituted for a histidine is selected from the group consisting of A, C, F M, V, W, and Y. In some embodiments, the variant CadA polypeptide is a variant of CadA from *E. coli* in which histidine at position H458 is substituted with another amino acid. In some embodiments, the amino acid that is substituted for an aspartate is selected from the group consisting of A, C, E, F, H, I, K, L, M, N, S, W, and Y. In some embodiments, the amino acid that is substituted for aspartate is selected from the group consisting of A, C, H, K, L, M, N, and S. In some embodiments, the variant CadA polypeptide is a variant of CadA from *E. coli* in which aspartate at position D457 is substituted with another amino acid.

In some embodiments, a variant CadA polypeptide of the invention has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of at 500 or more amino acids in length, or over the length of, the CadA polypeptide of SEQ ID NO:2; and has a substitution at an aspartic acid residue at position D457, or D460 as determined with reference to SEQ ID NO:2. In some embodiments, the substitution is D457A/C/E/F/H/I/K/L/M/N/S/W/Y, or D457A/C/H/K/L/M/N/S. In some embodiments, the substitution at position 460 is D460C/F/Q/I/S/V/W/Y, D460C/F/Q/I/S/V/W, or D460F/V/W/Y.

In some embodiments, a variant CadA polypeptide of the invention has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of at 500 or more amino acids in length, or over the length of, the CadA polypeptide of SEQ ID NO:3; and has a substitution at an aspartic acid residue at position D457, or D460 as determined with reference to SEQ ID NO:3. In some embodiments, the substitution is D457A/C/E/F/H/I/K/L/M/N/S/W/Y, or D457A/C/H/K/L/M/N/S. In some embodiments, the substitution at position 460 is D460C/F/Q/I/S/V/W/Y, D460C/F/Q/I/S/V/W, or D460F/V/W/Y.

In some embodiments, a variant CadA polypeptide of the invention has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of at 500 or more amino acids in length, or over the length of, the CadA polypeptide of SEQ ID NO:4; and has a substitution at an aspartic acid residue at position D457, or D460 as determined with reference to SEQ ID NO:4. In some embodiments, the substitution is D457A/C/E/F/H/I/K/L/M/N/S/W/Y, or D457A/C/H/K/L/M/N/S. In some embodiments, the substitution at position 460 is D460C/F/Q/I/S/V/W/Y, D460C/F/Q/I/S/V/W, or D460F/V/W/Y.

In some embodiments, a variant CadA polypeptide of the invention has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of at 500 or more amino acids in length, or over the length of, the CadA polypeptide of SEQ ID NO:5; and has a substitution at an aspartic acid residue at position D457, or D460 as determined with reference to SEQ ID NO:5. In some embodiments, the substitution is D457A/C/E/F/H/I/K/L/M/N/S/W/Y, or D457A/C/H/K/L/M/N/S. In some embodiments, the substitution at position 460 is D460C/F/Q/I/S/V/W/Y, D460C/F/Q/I/S/V/W, or D460F/V/W/Y.

Nucleic Acids Encoding CadA Variant Polypeptides

Isolation or generation of CadA polynucleotide sequences can be accomplished by a number of techniques. In some embodiments, oligonucleotide probes and based on the sequences disclosed here can be used to identify the desired polynucleotide in a cDNA or genomic DNA library from a desired bacteria species. Desired substitutions may be introduced into the CadA-encoding polynucleotide sequence using appropriate primers, e.g., as illustrated in the Examples section, to incorporate the desired changes into the polynucleotide sequence. For instance, PCR may be used to amplify the sequences of the genes directly from mRNA, from cDNA, from genomic libraries or cDNA libraries and to introduce desired substitutions.

Appropriate primers and probes for identifying a CadA polynucleotide in bacteria can be generated from comparisons of the sequences provided herein or generated based on a CadA polynucleotide sequence from another bacteria. For a general overview of PCR see PCR Protocols: A Guide to Methods and Applications. (Innis, M, Gelfand, D., Sninsky, J. and White, T., eds.), Academic Press, San Diego (1990). Illustrative primer sequences are shown in the Table of Primers in the Examples section.

Nucleic acid sequences encoding an acid decarboxylase polypeptide for use in the disclosure includes genes and gene products identified and characterized by techniques such as hybridization and/or sequence analysis using illustrative nucleic acid sequences, e.g., a cadA polynucleotide sequence of SEQ ID NO:1. In some embodiments, a host cell is genetically modified by introducing a nucleic acid sequence having at least 60% identity, or at least 70%, 75%, 80%, 85%, or 90% identity, or 95% identity, or greater, to an acid decarboxylase polynucleotide, e.g., a cadA polynucleotide of SEQ ID NO:1, wherein the nucleic acid comprises a codon that encodes the desired amino acid to be substituted.

Nucleic acid sequences encoding a CadA variant protein in accordance with the invention that confers increased production of an amino acid derivative, e.g., cadaverine, to a host cell, may additionally be codon-optimized for expression in a desired host cell. Methods and databases that can be employed are known in the art. For example, preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. See e.g., Henaut and Danchin in "*Escherichia coli* and *Salmonella*," Neidhardt, et al. Eds., ASM Pres, Washington D.C. (1996), pp. 2047-2066; Nucleic Acids Res. 20:2111-2118; Nakamura et al., 2000, *Nucl. Acids Res.* 28:292).

Preparation of Recombinant Vectors

Recombinant vectors for expression of a variant CadA protein can be prepared using methods well known in the art. For example, a DNA sequence encoding a CadA variant polypeptide, can be combined with transcriptional and other regulatory sequences which will direct the transcription of the sequence from the gene in the intended cells, e.g., bacterial cells such as *H. alvei, E. coli*, or *C. glutamicum*. In some embodiments, an expression vector that comprises an expression cassette that comprises the gene encoding the CadA variant polypeptide further comprises a promoter operably linked to the nucleic acid sequence encoding the CadA variant polypeptide. In other embodiments, a promoter and/or other regulatory elements that direct transcription of the cadA polynucleotide encoding a variant Cada polypeptide are endogenous to the host cell and an expression cassette comprising the cadA gene is introduced, e.g., by homologous recombination, such that the exogenous gene is operably linked to an endogenous promoter and is expression driven by the endogenous promoter.

As noted above, expression of the polynucleotide encoding a cadA variant polypeptide can be controlled by a number of regulatory sequences including promoters, which may be either constitutive or inducible; and, optionally, repressor sequences, if desired. Examples of suitable promoters, especially in a bacterial host cell, are the promoters obtained from the *E. coli* lac operon and other promoters derived from genes involved in the metabolism of other sugars, e.g., galactose and maltose. Additional examples include promoters such as the trp promoter, bla promoter bacteriophage lambda PL, and T5. In addition, synthetic promoters, such as the tac promoter (U.S. Pat. No. 4,551, 433), can be used. Further examples of promoters include *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes. Suitable promoters are also described in Ausubel and Sambrook & Russell, both supra. Additional promoters include promoters described by Jensen & Hammer, Appl. Environ. Microbiol. 64:82, 1998; Shimada, et al., J. Bacteriol. 186: 7112, 2004; and Miksch et al., Appl. Microbiol. Biotechnol. 69:312, 2005.

In some embodiments, a promoter that influences expression of a cadA gene encoding a CadA variant polypeptide of the invention may be modified to increase expression. For example, an endogenous CadA promoter may be replaced by a promoter that provides for increased expression compared to the native promoter.

An expression vector may also comprise additional sequences that influence expression of a polynucleotide encoding the CadA variant polypeptide. Such sequences include enhancer sequences, a ribosome binding site, or other sequences such as transcription termination sequences, and the like.

A vector expressing a polynucleotide encoding a CadA variant polypeptide of the invention may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Thus, an expression vector may additionally contain an element(s) that permits integration of the vector into the host's genome.

An expression vector of the invention preferably contains one or more selectable markers which permit easy selection of transformed hosts. For example, an expression vector may comprise a gene that confers antibiotic resistance (e.g., ampicillin, kanamycin, chloramphenicol or tetracycline resistance) to the recombinant host organism, e.g., a bacterial cell such as *E. coli*.

Although any suitable expression vector may be used to incorporate the desired sequences, readily available bacterial expression vectors include, without limitation: plasmids such as pSC101, pBR322, pBBR1MCS-3, pUR, pET, pEX, pMR100, pCR4, pBAD24, p15a, pACYC, pUC, e.g., pUC18 or pUC19, or plasmids derived from these plasmids; and bacteriophages, such as M13 phage and λ phage. One of ordinary skill in the art, however, can readily determine through routine experimentation whether any particular expression vector is suited for any given host cell. For example, the expression vector can be introduced into the host cell, which is then monitored for viability and expression of the sequences contained in the vector.

Expression vectors of the invention may be introduced into the host cell using any number of well-known methods, including calcium chloride-based methods, electroporation, or any other method known in the art.

Host Cells

The present invention provides for a genetically modified host cell that is engineered to express a CadA variant polypeptide of the invention. A genetically modified host strain of the present invention typically comprises at least one additional genetic modification to enhance production of an amino acid or amino acid derivative relative to a control strain that does not have the one additional genetic modification, e.g., a wildtype strain or a cell of the same strain without the one additional genetic modification. An "additional genetic modification to enhance production of an amino acid or amino acid derivative" can be any genetic modification. In some embodiments, the genetic modification is the introduction of a polynucleotide that expresses an enzyme involved in the synthesis of the amino acid or amino acid derivative. In some embodiments, the host cell comprises multiple modifications to increase production, relative to a wildtype host cell, of an amino acid or amino acid derivative.

In some aspects, genetic modification of a host cell to express a CadA variant polypeptide is performed in conjunction with modifying the host cell to overexpress one or more lysine biosynthesis polypeptides.

In some embodiments, a host cell may be genetically modified to express one or more polypeptides that affect lysine biosynthesis. Examples of lysine biosynthesis polypeptides include the *E. coli* genes SucA, Ppc, AspC, LysC, Asd, DapA, DapB, DapD, ArgD, DapE, DapF, LysA, Ddh, PntAB, CyoABE, GadAB, YbjE, GdhA, GltA, SucC, GadC, AcnB, PflB, ThrA, AceA, AceB, GltB, AceE, SdhA, MurE, SpeE, SpeG, PuuA, PuuP, and YgjG, or the corresponding genes from other organisms Such genes are known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes involved in cadaverine production. Illustrative genes encoding lysine biosynthesis polypeptides are provided below.

| Protein | Gene | EC Number | GenBank Accession No. |
| --- | --- | --- | --- |
| α-ketogultarate dehydrogenase (SucA) | sucA | 1.2.4.2 | YP_489005.1 |
| Phosphoenolpyruvate carboxylase (PPC) | ppc | 4.1.1.31 | AAC76938.1 |
| aspartate transaminase (AspC) | aspC | 2.6.1.1 | AAC74014.1 |
| aspartate kinase (LysC) | lysC | 2.7.2.4 | NP_418448.1 |
| aspartate semialdehyde dehydrogenase (Asd) | asd | 1.2.1.11 | AAC76458.1 |
| dihydrodipicolinate synthase (DapA) | dapA | 4.3.3.7 | NP_416973.1 |
| dihydropicolinate reductase (DapB) | dapB | 1.17.1.8 | AAC73142.1 |
| tetrahydrodipicoinate succinylase (DapD) | dapD | 2.3.1.117 | AAC73277.1 |
| N-succinyldiaminopimelate aminotransferase (ArgD) | argD | 2.6.1.11 | AAC76384.1 |
| N-succinyl-L-diaminopimelate deacylase (DapE) | dapE | 3.5.1.18 | AAC75525.1 |
| diaminopimelate epimerase (DapF) | dapF | 5.1.1.7 | AAC76812.2 |
| diaminopimelate decarboxylase (LysA) | lysA | 4.1.1.20 | AAC75877.1 |
| meso-diaminopimelate dehydrogenase (Ddh) | ddh | NA | P04964.1 |
| pyridine nucleotide transhydrogenase (PntAB) | pntAB | NA | AAC74675.1, AAC74674.1 |
| cytochrome O oxidase (CyoABE) | cyoABE | 1.10.3.10 | AAC73535.1, AAC73534.1, AAC73531.1 |
| glutamate decarboxylase (GadAB) | gadAB | 4.1.1.15 | AAC76542.1, AAC74566.1 |
| L-amino acid efflux transporter (YbjE) | ybjE | NA | AAC73961.2 |
| glutamate dehydrogenase (GdhA) | gdhA | 1.4.1.4 | AAC74831.1 |
| citrate synthase (GltA) | gltA | 2.3.3.1/2.3.3.16 | AAC73814.1 |
| succinyl-coA synthase (SucC) | sucC | 6.2.1.5 | AAC73822.1 |
| glutamate-GABA antiporter (GadC) | gadC | NA | AAC74565.1 |
| aconitase B (AcnB) | acnB | 4.2.1.99 | AAC73229.1 |
| pyruvate-formate lyase (PflB) | pflB | NA | AAC73989.1 |
| aspartate kinase/homoserine dehydrogenase (ThrA) | thrA | 2.7.2.4 | AAC73113.1 |
| isocitrate lyase (AceA) | aceA | 4.1.3.1 | AAC76985.1 |
| malate synthase (AceB) | aceB | 2.3.3.9 | AAC76984.1 |
| glutmate synthase (GltB) | gltB | 1.4.1.13 | AAC76244.2 |
| pyruvate dehydrogenase (AceE) | aceE | 1.2.4.1 | AAC73225.1 |
| succinate dehydrogenase (SdhA) | sdhA | 1.3.5.1 | AAC73817.1 |
| UDP-N-acetylmuramoyl-L-alanyl-D-glutamate:meso-diaminopimelate ligase (MurE) | murE | 6.3.2.13 | AAC73196.1 |
| putrescine/cadaverine aminopropyltransferase (SpeE) | speE | 2.5.1.16 | AAC73232.1 |
| spermidine acetyltransferase (SpeG) | speG | NA | AAC74656.1 |
| glutamate-putrescine/glutamate-cadaverine ligase (PuuA) | puuA | NA | AAC74379.2 |
| putrescine importer (PuuP) | puuP | NA | AAC74378.2 |
| putrescine/cadaverine aminotransferase (YgjG) | ygjG | 2.6.1.82 | AAC76108.3 |

In some embodiments, a host cell may be genetically modified to attenuate or reduce the expression of one or more polypeptides that affect lysine biosynthesis. Examples of such polypeptides include the *E. coli* genes Pck, Pgi, DeaD, CitE, MenE, PoxB, AceA, AceB, AceE, RpoC, and ThrA, or the corresponding genes from other organisms. Such genes are known in the art (see, e.g., Shah et al., J. Med. Sci. 2:152-157, 2002; Anastassiadia, S. Recent Patents on Biotechnol. 1: 11-24, 2007). See, also, Kind, et al., Appl. Microbiol. Biotechnol. 91: 1287-1296, 2011 for a review of genes attenuated to increase cadaverine production. Illustrative genes encoding polypeptides whose attenuation increases lysine biosynthesis are provided below.

| Protein | Gene | EC Number | GenBank Accession No. |
| --- | --- | --- | --- |
| PEP carboxykinase (Pck) | pck | 4.1.1.49 | NP_417862 |
| Glucose-6-phosphate isomerase (Pgi) | pgi | 5.3.1.9 | NP_418449 |
| DEAD-box RNA helicase (DeaD) | deaD | | NP_417631 |
| citrate lyase (CitE) | citE | 4.1.3.6/4.1.3.34 | NP_415149 |
| o-succinylbenzoate-CoA ligase (MenE) | menE | 6.2.1.26 | NP_416763 |
| pyruvate oxidase (PoxB) | poxB | 1.2.2.2 | NP_415392 |
| isocitrate lyase (AceA) | aceA | 4.1.3.1 | NP_418439 |
| malate synthase A (AceB) | aceB | 2.3.3.9 | NP_418438 |
| pyruvate dehydrogenase (aceE) | aceE | 1.2.4.1 | NP_414656 |
| RNA polymerase b' subunit (RpoC) | rpoC | 2.7.7.6 | NP_418415 |
| aspartokinase I (ThrA) | thrA | 2.7.2.4/1.1.1.3 | NP_414543 |

Nucleic acids encoding a lysine biosynthesis polypeptide may be introduced into the host cell along with a polynucleotide encoding a CadA variant polypeptide, e.g., encoded on a single expression vector, or introduced in multiple expression vectors at the same time. Alternatively, the host cell may be genetically modified to overexpress one or more lysine biosynthesis polypeptides before or after the host cells genetically modified to express a CadA variant polypeptide.

A host cell engineered to express a CadA variant polypeptide is typically a bacterial host cell. In typical embodiments, the bacterial host cell is a Gram-negative bacterial host cell. In some embodiments of the invention, the bacterium is an enteric bacterium. In some embodiments of the invention, the bacterium is a species of the genus *Corynebacterium, Escherichia, Pseudomonas, Zymomonas, Shewanella, Salmonella, Shigella, Enterobacter, Citrobacter, Cronobacter, Erwinia, Serratia, Proteus, Hafnia, Yersinia, Morganella, Edwardsiella,* or *Klebsiella* taxonomical classes. In some embodiments, the host cells are members of the genus *Escherichia, Hafnia,* or *Corynebacterium.* In some embodiments, the host cell is an *Escherichia coli, Hafnia alvei,* or *Corynebacterium glutamicum* host cell. In some embodiments, the host cell is *Escherichia coli.* In some embodiments, the host cell is *Hafnia alvei.* In some embodiments, the host cell is *Corynebacterium glutamicum.* In some embodiments, a genetically modified host cell from *E. coli* or *Corynebacterium* comprises a CadA variant polypeptide having an amino acid substitution in a region corresponding to amino acids 455 to 483 as determined with reference to SEQ ID NO:2, wherein the amino acid substitution does not include substitution at position D460 with reference to SEQ ID NO:2. In some embodiments, the genetically modified host cell comprises a CadA variant polypeptide, wherein the CadA variant comprise an amino acid substitution in a region corresponding to amino acids 455 to 483 at at least one of positions D457, H458, or D460 as determined with reference to SEQ ID NO:2, wherein the host cell is of a genus other than *Escherichia, Corynebacterium, Brevibacterium,* and *Microbacterium.*

In some embodiments, the host cell is a gram-positive bacterial host cell, such as a *Bacillus* sp., e.g., *Bacillus subtilis* or *Bacillus licheniformis*; or another *Bacillus* sp. such as *B. alcalophilus, B. aminovorans, B. amyloliquefaciens, B. caldolyticus, B. circulars, B. stearothermophilus, B. thermoglucosidasius, B. thuringiensis* or *B. vulgatis.*

Host cells modified in accordance with the invention can be screened for increased production of lysine or a lysine derivative, such as cadaverine, as described herein.

In some embodiments, a CadA variant polypeptide of the present invention may be recovered from a host cell that expresses the variant polypeptide. In some embodiments, the recovered variant protein may be immobilized onto a solid substrate or inert material to form an immobilized enzyme. In one embodiment, the immobilized enzyme may have improved operational stability than the soluble form of variant polypeptide.

Methods of Producing Lysine or a Lysine Derivative.

A host cell genetically modified to overexpress a CadA variant polypeptide of the invention can be employed to produce lysine or a derivative of lysine. In some embodiments, the host cell produces cadaverine. Thus, for example, to produce cadaverine, a host cell genetically modified to express a CadA variant polypeptide as described herein can be cultured under conditions suitable to allow expression of the polypeptide and expression of genes that encode the enzymes that are used to produce lysine and/or cadaverine. A host cell modified in accordance with the invention to express a CadA variant polypeptide provides a higher yield of cadaverine relative to a counterpart host cell that expresses native CadA. In some embodiments, the relative yield of cadaverine can be at least 125% as compared to the relative yield achieved with a counterpart hot cell expressing wild-type CadA Host cells may be cultured using well known techniques (see, e.g., the illustrative conditions provided in the examples section.

In some embodiments, host cells are cultured using nitrogen sources that are not salts (e g, ammonium sulfate or ammonium chloride), such as ammonia or urea. Host cells may be cultured at an alkaline pH during cell growth or enzyme production.

The lysine or lysine derivative can be separated and purified using known techniques. Lysine or lysine derivatives, e.g., cadverine, produced in accordance with the invention may then be used in any known process, e.g., to produce a polyamide.

In some embodiments, lysine may be converted to caprolactam using chemical catalysts or by using enzymes and chemical catalysts.

The present invention will be described in greater detail by way of specific examples. The following examples are offered for illustrative purposes, and are not intended to limit the invention in any manner. Those of skill in the art will readily recognize a variety of noncritical parameters, which can be changed or modified to yield essentially the same results.

EXAMPLES

Example 1: Calculation of pKa Values of Histidine Residues within CadA

There is research on various methods to calculate pKa values of a protein (Yang, et al., *Proteins* 15, 252-265, 1993; Van Vlijmen H W, et al., *Proteins* 33, 145-158, 1998; Rabenstein B & Knapp E W, *Biophysical Journal* 80, 1141-1150, 2001; Kieseritzky G & Knapp E W, *Proteins* 71, 1335-1348, 2008; Kilambi K P & Gray J J, *Biophysical J* 103, 587-595, 2012). The difference between computational and experimental pKa values for most amino acid residues tested in the literature is 0.5-0.75. Here, we used the linearized Poisson-Boltzmann equation-based pKa calculation method to predict the pKa values of the 24 histidine residues in the CadA protein. A summary of the pKa values calculated is presented in Table 1.

TABLE 1

Calculated pKa values of 24 histidine residues in the CadA protein of *E. coli*.

| Residue Number | pKa |
|---|---|
| 9 | 6.2 |
| 23 | 6.4 |
| 152 | 0.9 |
| 193 | >20.0 |
| 197 | −6.6 |
| 245 | 1.1 |
| 250 | 0.2 |
| 282 | 6.3 |
| 300 | −6.4 |
| 328 | >20.0 |
| 366 | 2.9 |
| 379 | −0.7 |
| 396 | 2.2 |
| 402 | −0.8 |
| 458 | 6.6 |
| 474 | −3.1 |
| 483 | −3.6 |
| 521 | 6.1 |
| 594 | 1.5 |
| 599 | 6.4 |
| 600 | 1.8 |
| 629 | 6.4 |
| 685 | 6.3 |
| 694 | 6.3 |

One histidine residue at position 458 with reference to SEQ ID NO:2 has a pKa value that is close to the pH at which CadA transitions between different oligomeric states. According to the literature (Kanjee U, et al. *The EMBO Journal*, 30, 931-944, 2011), CadA transitions from a state consisting of decamers and high-order oligomers to a state consisting of mostly dimers when the pH of the environment changes. Therefore, a change in pH is likely to affect H458 whose titratable groups have a pKa value similar to the pH where CadA oligomerization transition occurs.

H458 has an acidic amino acid located adjacent to it (D457) and a second acidic amino acid located two amino acid residues away (D460). The acid groups of D457 and D460 are titratable and could affect the pKa of H458 if they are a distance of less than 4 Å away from the side chain of H458. Analysis of the CadA X-ray crystal structure (PDB ID: 3N75) indicates that the titratable group of D457 is located 5.9 Å away from the side chain of H458, and that of D460 is located 6.6 Å away from the side chain of H458. However, rotation of the side chain at D457, H458, or D460 around the α-carbons can bring the titratable group of D457 2.7 Å away from H458, and as close as 1 Å away for D460. Both of these distances are within the 3 Å typically found between proton donors and acceptor groups in protein secondary structure elements. Typical distances between proton donor and acceptor pairs are 2.2 to 4 Å, where 2.2 Å is considered a strong interaction and 4 Å is considered a weak interaction. Interestingly, the side group of D457 is located on the same face as that of H458 even though they are adjacent amino acids. Typically, two adjacent amino acids have side groups that are located on opposite faces (i.e. facing opposite directions of each other). The side group of D460 is also located on the same face of H458, since they are separated by one amino acid. The orientations of the side groups suggest that D457 and D460 could affect the pKa of H458. We hypothesized that the amino acid positions 457, 458, and 460 are important for the function of the CadA polypeptide at different pH's. The following examples show that substitution of one or more amino acids having a titratable group with pKa values similar to the pH of CadA oligomerization transition can affect the activity of CadA. Specifically, the examples show amino acid substitution of a histidine residue at position 458 or amino acid substitution of an aspartate residues at positions 457 and/or 460 can increase production of cadaverine by host cells that are genetically modified to express the CadA variant polypeptide.

Example 2: Construction of Plasmid Vectors that Encode CadA

A plasmid vector containing wild-type *E. coli* cadA (SEQ ID NO: 1), which encodes the lysine decarboxylase CadA (SEQ ID NO: 2), was amplified from the *E. coli* MG1655 K12 genomic DNA using the PCR primers cadA-F and cadA-R (Table 11), digested using the restriction enzymes ScI and XbaI, and ligated into pUC18 to generate the plasmid pCIB60. The 5' sequence upstream of the cadA gene was optimized using the PCR primers cadA-F2 and cadA-R2 to create pCIB71.

Example 3: Construction of Plasmid Vectors that Encode CadA with a Mutation at D457

Primer pairs were designed to modify the amino acid at position 457 of the cadA gene in pCIB71 using Quickchange PCR. The mutations were verified using DNA sequencing, and the plasmids carrying each mutation at amino acid position 457 were labeled pCIB71-D457X, where X is the amino acid that replaced the aspartate residue.

Example 4: Construction of Plasmid Vectors that Encode CadA with a Mutation at H458

Primer pairs were designed to modify the amino acid at position 458 of the cadA gene in pCIB71 using Quickchange PCR. The mutations were verified using DNA sequencing, and the plasmids carrying each mutation at amino acid position 458 were labeled pCIB71-H458X, where X is the amino acid that replaced the histidine residue.

Example 5: Construction of Plasmid Vectors that Encode CadA with a Mutation at D460

Primer pairs were designed to modify the amino acid at position 460 of the cadA gene in pCIB71 using Quickchange PCR. The mutations were verified using DNA sequencing, and the plasmids carrying each mutation at amino acid position 460 were labeled pCIB71-D460X, where X is the amino acid that replaced the aspartate residue.

Example 6: Lysine Decarboxylase Activity of Mutant CadA Polypeptides with a D457X Mutation

*H. alvei* was transformed with pCIB71-D457X. Three single colonies from each transformation were grown overnight at 37° C. in 4 mL of LB medium with ampicillin (100 µg/mL). The following day, 0.7 mL of each overnight culture was added to 0.3 mL of lysine-HCl and PLP to a final concentration of 120 g/L and 0.1 mM, respectively. The final mixture was adjusted to pH 8.0 with 1M NaOH. Each mixture was incubated at 37° C. for 2 hours. Cadaverine production from each sample was quantified using NMR, and yield was calculated by dividing the molar amount of cadaverine produced by the molar amount of lysine added. The yield from each sample relative to the yield from *H. alvei* transformed with pCIB71 after 2 hours is presented in Table 2.

TABLE 2

Relative cadaverine yield at pH 8 by *H. alvei* strains expressing plasmids encoding CadA polypeptides with mutations at amino acid position 457.

| Plasmid | Relative Yield (%) |
| --- | --- |
| pCIB71 | 100 |
| pCIB71-D457A | 138 |
| pCIB71-D457C | 156 |
| pCIB71-D457E | 112 |
| pCIB71-D457F | 116 |
| pCIB71-D457G | 69 |
| pCIB71-D457H | 152 |
| pCIB71-D457I | 124 |
| pCIB71-D457K | 126 |
| pCIB71-D457L | 147 |
| pCIB71-D457M | 130 |
| pCIB71-D457N | 130 |
| pCIB71-D457P | 65 |
| pCIB71-D457Q | 0 |
| pCIB71-D457R | 0 |
| pCIB71-D457S | 170 |
| pCIB71-D457T | 73 |
| pCIB71-D457V | 0 |
| pCIB71-D457W | 117 |
| pCIB71-D457Y | 120 |

As shown in Table 2, several different mutations at amino acid position 457 improved the lysine decarboxylase yield relative to the wild-type CadA (pCIB71) at pH 8. The mutations D457A, D457C, D457H, D457K, D475L, D457M, D457N, and D457S increased yield by more than 25%. The mutations D457E, D457F, D457I, D457W, and D457Y also increased yield compared to the wild-type CadA. The mutations D457G, D457P, and D457T reduced yield. The mutations D457Q, D457R, and D457V eliminated lysine decarboxylase activity.

Example 7: Lysine Decarboxylase Activity of Mutant CadA Polypeptides with a H458X Mutation

*H. alvei* was transformed with pCIB71-H458X. Three single colonies from each transformation were grown overnight at 37° C. in 4 mL of LB medium with ampicillin (100 µg/mL). The following day, 0.7 mL of each overnight culture was added to 0.3 mL of lysine-HCl and PLP to a final concentration of 120 g/L and 0.1 mM, respectively. The final mixture was adjusted to pH 8.0 with 1M NaOH. Each mixture was incubated at 37° C. for 2 hours. Cadaverine production from each sample was quantified using NMR, and yield was calculated by dividing the molar amount of cadaverine produced by the molar amount of lysine added. The yield from each sample relative to the yield from *H. alvei* transformed with pCIB71 after 2 hours is presented in Table 3.

TABLE 3

Relative cadaverine yield at pH 8 by *H. alvei* strains expressing plasmids encoding CadA polypeptides with mutations at amino acid position 458.

| Plasmid | Relative Yield (%) |
| --- | --- |
| pCIB71 | 100 |
| pCIB71-H458A | 157 |
| pCIB71-H458C | 126 |
| pCIB71-H458D | 91 |
| pCIB71-H458E | 103 |
| pCIB71-H458F | 177 |
| pCIB71-H458G | 120 |
| pCIB71-H458I | 100 |
| pCIB71-H458K | 89 |
| pCIB71-H458L | 94 |
| pCIB71-H458M | 140 |
| pCIB71-H458N | 100 |
| pCIB71-H458P | 111 |
| pCIB71-H458Q | 91 |
| pCIB71-H458R | 88 |
| pCIB71-H458S | 0 |
| pCIB71-H458T | 105 |
| pCIB71-H458V | 137 |
| pCIB71-H458W | 165 |
| pCIB71-H458Y | 151 |

As shown in Table 3, several different mutations at amino acid position 458 improved the cadaverine yield relative to the wild-type CadA (pCIB71) at pH 8. The mutations H458A, H458C, H458F, H458M, H458V, H458W, and H458Y increased yield by more than 25%. The mutations H458G and H458P also increased yield compared to the wild-type CadA. The mutations H458D, H458E, H458K, H458L, H458N, H458Q, H458R, and H458T had little effect on yield. The mutation H458S eliminated lysine decarboxylase activity.

Example 8: Lysine decarboxylase activity of mutant CadA polypeptides with a D460X mutation

*H. alvei* was transformed with pCIB71-D460X. Three single colonies from each transformation were grown overnight at 37° C. in 4 mL of LB medium with ampicillin (100 µg/mL). The following day, 0.7 mL of each overnight culture was added to 0.3 mL of lysine-HCl and PLP to a final concentration of 120 g/L and 0.1 mM, respectively. The final mixture was adjusted to pH 8.0 with 1M NaOH. Each mixture was incubated at 37° C. for 2 hours. Cadaverine production from each sample was quantified using NMR, and yield was calculated by dividing the molar amount of cadaverine produced by the molar amount of lysine added. The yield from each sample relative to the yield from *H. alvei* transformed with pCIB71 after 2 hours is presented in Table 4.

TABLE 4

Relative cadaverine yield at pH 8 by *H. alvei* strains expressing plasmids encoding CadA polypeptides with mutations at amino acid position 460.

| Plasmid | Relative Yield (%) |
|---|---|
| pCIB71 | 100 |
| pCIB71-D460A | 93 |
| pCIB71-D460C | 168 |
| pCIB71-D460E | 71 |
| pCIB71-D460F | 152 |
| pCIB71-D460G | 86 |
| pCIB71-D460H | 77 |
| pCIB71-D460I | 169 |
| pCIB71-D460K | 69 |
| pCIB71-D460L | 50 |
| pCIB71-D460M | 97 |
| pCIB71-D460N | 0 |
| pCIB71-D460P | 66 |
| pCIB71-D460Q | 155 |
| pCIB71-D460R | 0 |
| pCIB71-D460S | 159 |
| pCIB71-D460T | 75 |
| pCIB71-D460V | 175 |
| pCIB71-D460W | 163 |
| pCIB71-D460Y | 102 |

As shown in Table 4, several mutations at amino acid position 460 improved the activity of the CadA polypeptide at pH 8.0. The mutations D460C, D460F, D460I, D460Q, D460S, D460I, D460V, and D460W increased relative cadaverine yield by more than 25%. The mutations D460A, D460G, D460M, and D460Y had little effect on yield. The mutations D460N and D460R eliminated activity. The remaining mutations D460E, D460H, D460K, D460L, D460P, and D460T had a negative effect on cadaverine yield.

Example 9: In Vitro Kinetic Analysis of Wild-Type and Mutant CadA Polypeptides at Alkaline pH Conditions According to the literature, the activity of CadA at pH 8 is significantly less than its activity at pH 6 due to a structural change from a high oligomer state to a dimer state. The activity of the wild-type and mutant CadA polypeptides was compared at pH 6 and pH 8, in order to determine whether the mutations can increase the tolerance of the CadA polypeptide to alkaline conditions.

100 mL samples of *H. avlei* transformed with pCIB71, pCIB71-D457S, pCIB71-H458F, or pCIB71-D460V were lysed with a french press. The lysed samples were centrifuged, and the supernatant was separated from the pellet in order to perform in vitro experiments. Each reaction was performed in Tris-HCl buffer (50 mM Tris-HCl either pH 6 or 8, 25 mM NaCl, 2 mM EDTA) with 120 g/L lysine-HCl and 0.1 mM PLP. The reaction rate of each lysed sample was measured using NMR by sampling the amount of lysine converted in the presence of PLP into cadaverine every 1.6 minutes for a total of 20 minutes, and taking the slope of the linear portion of the yield curve. The samples were diluted so that the reaction rate per volume (mmol/min/mL, U) of lysed sample was the same. The samples were diluted so that U of each sample was 0.5. The kinetic constant Vmax for lysine of each lysed samples was measured using the same U at an initial pH of either 6 or pH 8. By normalizing for U, the concentration of active enzyme in each sample is the same. The results of the kinetic analysis of the two samples are shown in Table 5.

TABLE 5

Kinetic analysis of normalized Vmax of lysed samples of *H. avlei* expressing plasmids encoding wild-type or mutant CadA polypeptides under different pH conditions.

| pH | pCIB71 | pCIB71-D457S | pCIB71-H458F | pCIB71-D460V |
|---|---|---|---|---|
| 6 | 100% | 101% | 100% | 102% |
| 8 | 49% | 72% | 70% | 70% |

In accordance with the literature, wild-type CadA (pCIB71) lost a significant amount of activity at pH 8 compared to pH 6. The reduction in activity at pH 8 compared to pH 6 was 51%. Surprisingly, the mutant CadA polypeptides (D457S, H458F, and D460V) all showed greater activity at pH 8 compared to the wild-type CadA.

Example 10: Time Course of Cadaverine Production by Mutant CadA Polypeptide

*H. avlei* was transformed with either pCIB71 or pCIB71-D460V. Three single colonies from each transformation were grown overnight at 37° C. in 10 mL of LB medium with ampicillin (100 μg/mL). The following day, each overnight culture was aliquoted into 8 separate test tubes representing a different time point, each test tube containing 0.7 mL of an overnight culture, 0.3 mL of lysine-HCl (final concentration 120 g/L), and PLP (final concentration 0.1 mM). The final mixture in each test tube was adjusted to pH 8.0 with 1M NaOH. Each mixture was incubated at 37° C. and shaken at 220 rpm. At each time point, a sample for each colony was removed for analysis. Cadaverine production from each sample was quantified using NMR, and yield was calculated by dividing the molar amount of cadaverine produced by the molar amount of lysine added. The yield at each time point is presented in Table 6.

TABLE 6

Cadaverine yield of *H. avlei* expressing plasmids encoding wild-type and mutant CadA polypeptides during different time points at pH 8.0.

| Time points (min) | pCIB71 | pCIB71-D460V |
|---|---|---|
| 60 | 7.22 | 51.6 |
| 120 | 17.5 | 77.3 |
| 180 | 30.7 | 97.5 |
| 240 | 50.4 | 98.1 |
| 300 | 73.4 | 100 |
| 360 | 85.8 | 100 |
| 420 | 86.0 | 100 |
| 480 | 88.5 | 100 |

As shown in Table 6, lysine is converted into cadaverine at pH 8.0 much faster by cells overexpressing the mutant CadA D460V compared to the wild-type CadA (pCIB71). After 240 minutes, the mutant CadA has converted 98.1% of the lysine, whereas the wild-type CadA has only completed 50% of the lysine into cadaverine. After 300 minutes, the mutant CadA completed the lysine to cadaverine conversion, whereas the wild-type CadA did not complete the conversion even after 480 minutes.

TABLE 7

Table of plasmids and strains used in Examples.

| Host | Protein(s) Overexpressed | Plasmid |
|---|---|---|
| *Hafnia alvei* | CadA | pCIB71 |
| *Hafnia alvei* | CadA D457A | pCIB71-D457A |
| *Hafnia alvei* | CadA D457C | pCIB71-D457C |
| *Hafnia alvei* | CadA D457E | pCIB71-D457E |
| *Hafnia alvei* | CadA D457F | pCIB71-D457F |
| *Hafnia alvei* | CadA D457G | pCIB71-D457G |
| *Hafnia alvei* | CadA D457H | pCIB71-D457H |
| *Hafnia alvei* | CadA D457I | pCIB71-D457I |
| *Hafnia alvei* | CadA D457K | pCIB71-D457K |
| *Hafnia alvei* | CadA D457L | pCIB71-D457L |
| *Hafnia alvei* | CadA D457M | pCIB71-D457M |
| *Hafnia alvei* | CadA D457N | pCIB71-D457N |
| *Hafnia alvei* | CadA D457P | pCIB71-D457P |
| *Hafnia alvei* | CadA D457Q | pCIB71-D457Q |
| *Hafnia alvei* | CadA D457R | pCIB71-D457R |
| *Hafnia alvei* | CadA D457S | pCIB71-D457S |
| *Hafnia alvei* | CadA D457T | pCIB71-D457T |
| *Hafnia alvei* | CadA D457V | pCIB71-D457V |
| *Hafnia alvei* | CadA D457W | pCIB71-D457W |
| *Hafnia alvei* | CadA D457Y | pCIB71-D457Y |
| *Hafnia alvei* | CadA H458A | pCIB71-H458A |
| *Hafnia alvei* | CadA H458C | pCIB71-H458C |
| *Hafnia alvei* | CadA H458D | pCIB71-H458D |
| *Hafnia alvei* | CadA H458E | pCIB71-H458E |
| *Hafnia alvei* | CadA H458F | pCIB71-H458F |
| *Hafnia alvei* | CadA H458G | pCIB71-H458G |
| *Hafnia alvei* | CadA H458I | pCIB71-DH58I |
| *Hafnia alvei* | CadA H458K | pCIB71-H458K |
| *Hafnia alvei* | CadA H458L | pCIB71-H458L |
| *Hafnia alvei* | CadA H458M | pCIB71-H458M |
| *Hafnia alvei* | CadA H458N | pCIB71-H458N |
| *Hafnia alvei* | CadA H458P | pCIB71-H458P |
| *Hafnia alvei* | CadA H458Q | pCIB71-H458Q |
| *Hafnia alvei* | CadA H458R | pCIB71-H458R |
| *Hafnia alvei* | CadA H458S | pCIB71-H458S |
| *Hafnia alvei* | CadA H458T | pCIB71-H458T |
| *Hafnia alvei* | CadA H458V | pCIB71-H458V |
| *Hafnia alvei* | CadA H458W | pCIB71-H458W |
| *Hafnia alvei* | CadA H458Y | pCIB71-H458Y |
| *Hafnia alvei* | CadA D460A | pCIB71-D460A |
| *Hafnia alvei* | CadA D460C | pCIB71-D460C |
| *Hafnia alvei* | CadA D460E | pCIB71-D460E |
| *Hafnia alvei* | CadA D460F | pCIB71-D460F |
| *Hafnia alvei* | CadA D460G | pCIB71-D460G |
| *Hafnia alvei* | CadA D460H | pCIB71-D460H |
| *Hafnia alvei* | CadA D460I | pCIB71-D460I |
| *Hafnia alvei* | CadA D460K | pCIB71-D460K |
| *Hafnia alvei* | CadA D460L | pCIB71-D460L |
| *Hafnia alvei* | CadA D460M | pCIB71-D460M |
| *Hafnia alvei* | CadA D460N | pCIB71-D460N |
| *Hafnia alvei* | CadA D460P | pCIB71-D460P |
| *Hafnia alvei* | CadA D460Q | pCIB71-D460Q |
| *Hafnia alvei* | CadA D460R | pCIB71-D460R |
| *Hafnia alvei* | CadA D460S | pCIB71-D460S |
| *Hafnia alvei* | CadA D460T | pCIB71-D460T |
| *Hafnia alvei* | CadA D460V | pCIB71-D460V |
| *Hafnia alvei* | CadA D460W | pCIB71-D460W |
| *Hafnia alvei* | CadA D460Y | pCIB71-D460Y |

TABLE 8

Table of primer sequences used in Examples.

| Name | Sequence (5'-3') |
|---|---|
| cadA-F | GGCGAGCTCACACAGGAAACAGACCATGAACGTTATTGCAATATTGAATCAC |
| cadA-R | GGCTCTAGACCACTTCCCTTGTACGAGC |
| cadA-F2 | ATTTCACACAGGAAACAGCTATGAACGTTATTGCAATATTGAAT |
| cadA-R2 | AGCTGTTTCCTGTGTGAAAT |
| D457C-F | TGGCAGCCGTGTCATATCGATACGACTGAATG |
| D457C-R | ATCGATATGACACGGCTGCCATACATCAAAG |
| D457A-F | TGGCAGCCGGCGCATATCGATACGACTGAATG |
| D457A-R | ATCGATATGCGCCGGCTGCCATACATCAAAG |
| D457H-F | TGGCAGCCGCATCATATCGATACGACTGAATG |
| D457H-R | ATCGATATGATGCGGCTGCCATACATCAAAG |
| D457K-F | TGGCAGCCGAAACATATCGATACGACTGAATG |
| D457K-R | ATCGATATGTTTCGGCTGCCATACATCAAAG |
| D457R-F | TGGCAGCCGCGTCATATCGATACGACTGAATG |
| D457R-R | ATCGATATGACGCGGCTGCCATACATCAAAG |
| D457L-F | TGGCAGCCGCTGCATATCGATACGACTGAATG |
| D457L-R | ATCGATATGCAGCGGCTGCCATACATCAAAG |
| D457S-F | TGGCAGCCGAGCCATATCGATACGACTGAATG |
| D457S-R | ATCGATATGGCTCGGCTGCCATACATCAAAG |
| D457P-F | TGGCAGCCGCCGCATATCGATACGACTGAATG |
| D457P-R | ATCGATATGCGGCGGCTGCCATACATCAAAG |
| D457E-F | TGGCAGCCGGAACATATCGATACGACTGAATG |
| D457E-R | ATCGATATGTTCCGGCTGCCATACATCAAAG |
| D457T-F | TGGCAGCCGACCCATATCGATACGACTGAATG |
| D457T-R | ATCGATATGGGTCGGCTGCCATACATCAAAG |
| D457Y-F | TGGCAGCCGTATCATATCGATACGACTGAATG |
| D457Y-R | ATCGATATGATACGGCTGCCATACATCAAAG |
| D457G-F | TGGCAGCCGGGCCATATCGATACGACTGAATG |
| D457G-R | ATCGATATGGCCCGGCTGCCATACATCAAAG |
| D457V-F | TGGCAGCCGGTGCATATCGATACGACTGAATG |
| D457V-R | ATCGATATGCACCGGCTGCCATACATCAAAG |
| D457F-F | TGGCAGCCGTTTCATATCGATACGACTGAATG |
| D457F-R | ATCGATATGAAACGGCTGCCATACATCAAAG |
| D457N-F | TGGCAGCCGAACCATATCGATACGACTGAATG |
| D457N-R | ATCGATATGGTTCGGCTGCCATACATCAAAG |
| D457Q-F | TGGCAGCCGCAGCATATCGATACGACTGAATG |
| D457Q-R | ATCGATATGCTGCGGCTGCCATACATCAAAG |
| D457I-F | TGGCAGCCGATCCATATCGATACGACTGAATG |
| D457I-R | ATCGATATGGATCGGCTGCCATACATCAAAG |
| D457M-F | TGGCAGCCGATGCATATCGATACGACTGAATG |
| D457M-R | ATCGATATGCATCGGCTGCCATACATCAAAG |
| D457W-F | TGGCAGCCGTGGCATATCGATACGACTGAATG |

TABLE 8-continued

Table of primer sequences used in Examples.

| Name | Sequence (5'-3') |
|---|---|
| D457W-R | ATCGATATGCCACGGCTGCCATACATCAAAG |
| D460C-F | GGATCATATCTGCACGACTGAATGCTGGCCGCTGCGTTC |
| D460C-R | ATTCAGTCGTGCAGATATGATCCGGCTGCCATACATCAA |
| D460H-F | GGATCATATCCATACGACTGAATGCTGGCCGCTGCGTTC |
| D460H-R | ATTCAGTCGTATGGATATGATCCGGCTGCCATACATCAA |
| D460K-F | GGATCATATCAAAACGACTGAATGCTGGCCGCTGCGTTC |
| D460K-R | ATTCAGTCGTTTTGATATGATCCGGCTGCCATACATCAA |
| D460R-F | GGATCATATCCGTACGACTGAATGCTGGCCGCTGCGTTC |
| D460R-R | ATTCAGTCGTACGGATATGATCCGGCTGCCATACATCAA |
| D460L-F | GGATCATATCCTGACGACTGAATGCTGGCCGCTGCGTTC |
| D460L-R | ATTCAGTCGTCAGGATATGATCCGGCTGCCATACATCAA |
| D460S-F | GGATCATATCAGCACGACTGAATGCTGGCCGCTGCGTTC |
| D460S-R | ATTCAGTCGTGCTGATATGATCCGGCTGCCATACATCAA |
| D460P-F | GGATCATATCCCGACGACTGAATGCTGGCCGCTGCGTTC |
| D460P-R | ATTCAGTCGTCGGGATATGATCCGGCTGCCATACATCAA |
| D460E-F | GGATCATATCGAAACGACTGAATGCTGGCCGCTGCGTTC |
| D460E-R | ATTCAGTCGTTTCGATATGATCCGGCTGCCATACATCAA |
| D460T-F | GGATCATATCACCACGACTGAATGCTGGCCGCTGCGTTC |
| D460T-R | ATTCAGTCGTGGTGATATGATCCGGCTGCCATACATCAA |
| D460Y-F | GGATCATATCTATACGACTGAATGCTGGCCGCTGCGTTC |
| D460Y-R | ATTCAGTCGTATAGATATGATCCGGCTGCCATACATCAA |
| D460A-F | GGATCATATCGCGACGACTGAATGCTGGCCGCTGCGTTC |
| D460A-R | ATTCAGTCGTCGCGATATGATCCGGCTGCCATACATCAA |
| D460G-F | GGATCATATCGGCACGACTGAATGCTGGCCGCTGCGTTC |
| D460G-R | ATTCAGTCGTGCCGATATGATCCGGCTGCCATACATCAA |
| D460V-F | GGATCATATCGTGACGACTGAATGCTGGCCGCTGCGTTC |
| D460V-R | ATTCAGTCGTCACGATATGATCCGGCTGCCATACATCAA |
| D460E-F | GGATCATATCTTTACGACTGAATGCTGGCCGCTGCGTTC |
| D460E-R | ATTCAGTCGTAAAGATATGATCCGGCTGCCATACATCAA |
| D460N-F | GGATCATATCAACACGACTGAATGCTGGCCGCTGCGTTC |
| D460N-R | ATTCAGTCGTGTTGATATGATCCGGCTGCCATACATCAA |
| D460Q-F | GGATCATATCCAGACGACTGAATGCTGGCCGCTGCGTTC |
| D460Q-R | ATTCAGTCGTCTGGATATGATCCGGCTGCCATACATCAA |
| D460I-F | GGATCATATCATCACGACTGAATGCTGGCCGCTGCGTTC |
| D460I-R | ATTCAGTCGTGATGATATGATCCGGCTGCCATACATCAA |
| D460M-F | GGATCATATCATGACGACTGAATGCTGGCCGCTGCGTTC |
| D460M-R | ATTCAGTCGTCATGATATGATCCGGCTGCCATACATCAA |
| D460W-F | GGATCATATCTGGACGACTGAATGCTGGCCGCTGCGTTC |
| D460W-R | ATTCAGTCGTCCAGATATGATCCGGCTGCCATACATCAA |
| H458F-F | ATGGCAGCCGGATTTCATCGATACGACTGAATGCTG |
| H458F-R | AGTCGTATCGATGAAATCCGGCTGCCATACATCAAAGAAC |
| H458L-F | ATGGCAGCCGGATCTAATCGATACGACTGAATGCTG |
| H458L-R | AGTCGTATCGATTAGATCCGGCTGCCATACATCAAAGAAC |
| H458S-F | ATGGCAGCCGGATTGAATCGATACGACTGAATGCTG |
| H458S-R | AGTCGTATCGATTCAATCCGGCTGCCATACATCAAAGAAC |
| H458Y-F | ATGGCAGCCGGATTACATCGATACGACTGAATGCTG |
| H458Y-R | AGTCGTATCGATGTAATCCGGCTGCCATACATCAAAGAAC |
| H458P-F | ATGGCAGCCGGATCCAATCGATACGACTGAATGCTG |
| H458P-R | AGTCGTATCGATTGGATCCGGCTGCCATACATCAAAGAAC |
| H458Q-F | ATGGCAGCCGGATCAAATCGATACGACTGAATGCTG |
| H458Q-R | AGTCGTATCGATTTGATCCGGCTGCCATACATCAAAGAAC |
| H458R-F | ATGGCAGCCGGATCGTATCGATACGACTGAATGCTG |
| H458R-R | AGTCGTATCGATACGATCCGGCTGCCATACATCAAAGAAC |
| H458W-F | ATGGCAGCCGGATTGGATCGATACGACTGAATGCTG |
| H458W-R | AGTCGTATCGATCCAATCCGGCTGCCATACATCAAAGAAC |
| H458I-F | ATGGCAGCCGGATATCATCGATACGACTGAATGCTG |
| H458I-R | AGTCGTATCGATGATATCCGGCTGCCATACATCAAAGAAC |
| H458T-F | ATGGCAGCCGGATACTATCGATACGACTGAATGCTG |
| H458T-R | AGTCGTATCGATAGTATCCGGCTGCCATACATCAAAGAAC |
| H458D-F | ATGGCAGCCGGATGATATCGATACGACTGAATGCTG |
| H458D-R | AGTCGTATCGATATCATCCGGCTGCCATACATCAAAGAAC |
| H458K-F | ATGGCAGCCGGATAAGATCGATACGACTGAATGCTG |
| H458K-R | AGTCGTATCGATCTTATCCGGCTGCCATACATCAAAGAAC |
| H458N-F | ATGGCAGCCGGATAACATCGATACGACTGAATGCTG |
| H458N-R | AGTCGTATCGATGTTATCCGGCTGCCATACATCAAAGAAC |
| H458E-F | ATGGCAGCCGGATGAAATCGATACGACTGAATGCTG |
| H458E-R | AGTCGTATCGATTTCATCCGGCTGCCATACATCAAAGAAC |
| H458A-F | ATGGCAGCCGGATGCTATCGATACGACTGAATGCTG |
| H458A-R | AGTCGTATCGATAGCATCCGGCTGCCATACATCAAAGAAC |
| H458G-F | ATGGCAGCCGGATGGTATCGATACGACTGAATGCTG |
| H458G-R | AGTCGTATCGATACCATCCGGCTGCCATACATCAAAGAAC |
| H458V-F | ATGGCAGCCGGATGTAATCGATACGACTGAATGCTG |
| H458V-R | AGTCGTATCGATTACATCCGGCTGCCATACATCAAAGAAC |
| H458M-F | ATGGCAGCCGGATATGATCGATACGACTGAATGCTG |
| H458M-R | AGTCGTATCGATCATATCCGGCTGCCATACATCAAAGAAC |

Illustrative sequences:

SEQ ID NO: 1 Escherichia coli cadA nucleic acid sequence
ATGAACGTTATTGCAATATTGAATCACATGGGGGTTTATTTTAAAGAAGAACCCATCCGTGAACTTCATCGCGCGCTTGAA
CGTCTGAACTTCCAGATTGTTTACCCGAACGACCGTGACGACTTATTAAAACTGATCGAAAACAATGCGCGTCTGTGCGGC
GTTATTTTTGACTGGGATAAATATAATCTCGAGCTGTGCGAAGAAATTAGCAAAATGAACGAGAACCTGCCGTTGTACGCG
TTCGCTAATACGTATTCCACTCTCGATGTAAGCCTGAATGACCTGCGTTTACAGATTAGCTTCTTTGAATATGCGCTGGGTG
CTGCTGAAGATATTGCTAATAAGATCAAGCAGACCACTGACGAATATATCAACACTATTCTGCCTCCGCTGACTAAAGCAC
TGTTTAAATATGTTCGTGAAGGTAAATATACTTTCTGTACTCCTGGTCACATGGGCGGTACTGCATTCCAGAAAAGCCCGG
TAGGTAGCCTGTTCTATGATTTCTTTGGTCCGAATACCATGAAATCTGATATTTCCATTTCAGTATCTGAACTGGGTTCTCTG
CTGGATCACAGTGGTCCACACAAAGAAGCAGAACAGTATATCGCTCGCGTCTTTAACGCAGACCGCAGCTACATGGTGAC
CAACGGTACTTCCACTGCGAACAAAATTGTTGGTATGTACTCTGCTCCAGCAGGCAGCACCATTCTGATTGACCGTAACTG
CCACAAATCGCTGACCCACCTGATGATGATGAGCGATGTTACGCCAATCTATTTCCGCCCGACCCGTAACGCTTACGGTAT
TCTTGGTGGTATCCCACAGAGTGAATTCCAGCACGCTACCATTGCTAAGCGCGTGAAAGAAACACCAAACGCAACCTGGC
CGGTACATGCTGTAATTACCAACTCTACCTATGATGGTCTGCTGTACAACACCGACTTCATCAAGAAACACTGGATGTGA
AATCCATCCACTTTGACTCCGCGTGGGTGCCTTACACCAACTTCTCACCGATTTACGAAGGTAAATGCGGTATGAGCGGTG
GCCGTGTAGAAGGGAAAGTGATTTACGAAACCCAGTCCACTCACAAACTGCTGGCGGCGTTCTCTCAGGCTTCCATGATCC
ACGTTAAAGGTGACGTAAACGAAGAAACCTTTAACGAAGCCTACATGATGCACACCACCACTTCTCCGCACTACGGTATC
GTGGCGTCCACTGAAACCGCTGCGGCGATGATGAAAGGCAATGCAGGTAAGCGTCTGATCAACGGTTCTATTGAACGTGC
GATCAAATTCCGTAAAGAGATCAAACGTCTGAGAACGGAATCTGATGGCTGGTTCTTTGATGTATGGCAGCCGGATCATAT
CGATACGACTGAATGCTGGCCGCTGCGTTCTGACAGCACCTGGCACGGCTTCAAAAACATCGATAACGAGCACATGTATCT
TGACCCGATCAAAGTCACCCTGCTGACTCCGGGGATGGAAAAAGACGGCACCATGAGCGACTTTGGTATTCCGGCCAGCA
TCGTGGCGAAATACCTCGACGAACATGGCATCGTTGTTGAGAAAACCGGTCCGTATAACCTGCTGTTCCTGTTCAGCATCG
GTATCGATAAGACCAAAGCACTGAGCCTGCTGCGTGCTCTGACTGACTTTAAACGTGCGTTCGACCTGAACCTGCGTGTGA
AAAACATGCTGCCGTCTCTGTATCGTGAAGATCCTGAATTCTATGAAAACATGCGTATTCAGGAACTGGCTCAGAATATCC
ACAAACTGATTGTTCACCACAATCTGCCGGATCTGATGTATCGCGCATTTGAAGTGCTGCCGACGATGGTAATGACTCCGT
ATGCTGCATTCCAGAAAGAGCTGCACGGTATGACCGAAGAAGTTTACCTCGACGAAATGGTAGGTCGTATTAACGCCAAT
ATGATCCTTCCGTACCCGCCGGGAGTTCCTCTGGTAATGCCGGGTGAAATGATCACCGAAGAAAGCCGTCCGGTTCTGGAG
TTCCTGCAGATGCTGTGTGAAATCGGCGCTCACTATCCGGGCTTTGAAACCGATATTCACGGTGCATACCGTCAGGCTGAT
GGCCGCTATACCGTTAAGGTATTGAAAGAAGAAAGCAAAAAATAA SEQ ID NO: 2 CadA polypeptide sequence
MNVIAILNHMGVYFKEEPIRELHRALERLNFQIVYPNDRDDLLKLIENNARLCGVIEDWDKYNLELCEEISKMNENLPLYAFANT
YSTLDVSLNDLRLQISFFEYALGAAEDIANKIKQTTDEYINTILPPLIKALFKYVREGKYTECTPGHMGGTAFQKSPVGSLEYDFF
GPNTMKSDISISVSELGSLLDHSGPHKEAEQYIARVFNADRSYMVINGTSTANKIVGMYSAPAGSTILIDRNCHKSLTHLMMIMS
DVTPIYFRPTRNAYGILGGIPQSEFQHATIAKRVKETPNATWPVHAVITNSTYDGLLYNTDFIKKILDVKSIHFDSAWVPYINFSPI
YEGKCGMSSGGRVEGKVIYETQSTHKLLAAFSQASMIHVKGDVNEETFNEAYMIMHTTTSPHYGIVASTETAAAMMKGNAGKRL
INGSIERAIKFRKEIKRLRTESDGWFFDVWQPDHIDTTECWPLRSDSTWHGFKNIDNEHMYLDPIKVTLLTPGMEKDGTMSDFGI
PASIVAKYLDEHGIVVEKTGPYNLLFLFSIGIDKTKALSLLRALTDFKRAFDLNLRVKNMLPSLYREDPEFYENMRIQELAQNIHK
LIVHHNLPDLMYRAFEVLPTMVMTPYAAFQKELHGMTEEVYLDEMVGRINANMILPYPPGVPLVMPGEMITEESRPVLEFLQM
LCEIGAHYPGFETDRIGAYRQADGRYTVKVLKEESKK SEQ ID NO: 3 Polypeptide from Klebsiella homologous to E. coli CadA
MNVIAIMNHMGVYFKEEPIRELHRALERLDFRIVYPNDRDDLLKLIENNSRLCGVIFDWDKYNLELCEEISKMNEYMPLYAFAN
TYSTLDVSLNDLRMQVRFFEYALGAAEDIANKIKQNTDEYIDTILPPLTKALFKYVREGKYTFCTPGHMGGTAFQKSPVGSIFYD
FFGPNTMKSDISISVSELGSLLDHSGPHKEALEYIARVFNAERSYMVINGTSTANKIVGMYSAPAGSTVLIDRNCHKSLTHLMM
MSDITPIYFRPTRNAYGILGGIPQSEFQHATIAKRVKETPNATWPVHAVITNSTYDGLLYNTDFIKKILDVKSIHFDSAWVPYINF
SPIYEGKCGMSSGGRVEGKVIYETQSTHKLLAAFSQASMIHVKGDVNEETFNEAYMIMHTTTSPHYGIVASTETAAAMMKGNAG
KRLIDGSIERSIKFRKEIKRLKGESDGWFFDVWQPEHIDGPECWPLRSDSAWHGFKNIDNEHMYLDPIKVTLLTPGMKKDGTMD
DFGIPASIVAKYLDEHGIVVEKTGPYNLLFLFSIGIDKTKALSLLRALTDFKRAFDLNLRVKNMLPSLYREDPEFYENMRIQDLAQ
NIHKLIEHHNLPDLMTRAFEVLPSMVMTPYAAFQKELHGQTEEVYLEEMVGRVNANMILPYPPGVPLVMPGEMITEESRPVLEF
LQMLCEIGAHYPGFETDIHGAYRQADGRYTVKVLKEENNK SEQ ID NO: 4 Polypeptide from Enterobacteriaceae homologous to E. coli CadA
MNVIAIMNHMGVYFKEEPIRELHRALERLDFRIVYPNDRDDLLKLIENNSRLCGVIFDWDKYNLELCEEISKMNEYMPLYAFAN
TYSTLDVSLNDLRMQVRFFEYALGAAEDIANKIKQNTDEYIDTILPPLTKALFKYVREGKYTFCTPGHMGGTAFQKSPVGSIFYD
FFGSNTMKSDISISVSELGSLLDHSGPHKEALEYIARVFNAERSYMVINGTSTANKIVGMYSAPAGSTVLIDRNCHKSLTHLMM
MSDITPIYFRPTRNAYGILGGIPQSEFQHATIAKRVKETPNATWPVHAVITNSTYDGLLYNTDFIKKILDVKSIHFDSAWVPYINF
SPIYEGKCGMSSGGRVEGKVIYETQSTHKLLAAFSQASMIHVKGDVNEETFNEAYMMHTTTSPHYGIVASTETAAAMMKGNAG
KRLIDGSIERSIKFRKEIKRLKGESDGWFFDVWQPEHIDGPECWPIRSDSAWHGFKNIDNEHMYLDPIKVTLLTPGMKKDGTMD
DFGIPASIVAKYLDEHGIVVEKTGPYNLLFLFSIGIDKTKALSLLRALTDFKRAFDLNLRVKNMLPSLYREDPEFYENMRIQDLAQ
NIHKLIEHHNLPDLMTRAFEVLPSMVMTPYAAFQKELHGQTEEVYLEEMVGRVNANMILPYPPGVPLVMPGEMITEESRPVLEF
LQMLCEIGAHYPGFETDIHGAYRQADGRYTVKVLKEENNK SEQ ID NO: 5 Polypeptide from Salmonella enterica homologous to E. coli CadA
MNVIAIMNHMGVYFKEEPIRELHRALEGLNFRIVYPNDREDLLKLIENNSRLCGVIFDWDKYNLELCEEISKLNEYMPLYAFANS
YSTLDVSLNDLRMQVRFFEYALGAATDIAAKIRQNTDEYIDNILPPLTKALFKYVREGKYTFCTPGHMGGTAFQKSPVGSIFYDF
FGPNTMKSDISISVSELGSLLDHSGPHKEALEYIARVFNAERSYMVINGTSTANKIVGMYSAPAGSTVLIDRNCHKSLTHLMMM
SDITPIYFRPTRNAYGILGGIPQSEFQHATIAKRVKETPNATWPVHAVITNSTYDGLLYNTDYIKKILDVKSIHFDSAWVPYINFSP
IYQGKCGMSGDRVEGKIIYETQSTHKLLAAFSQASMRIVKGDINEETFNEAYMMHTTSPHYGIVASTETAAAMMKGNAGKRLI
NGSIERAIKFRKEIKRLKSESDGWFFDVWQPEHIDGAECWPLRSDSAWHGFKNIDNEHMYLDPIKVTILTPGMKKDGTMDEFGIP
ASLVAKYLDERGIIVEKTGPYNLLFLFSIGIDKTKALSLLRALTEFKRAFDLNLRVKNILPALYREAPEFYENMRIQELAQNIHKLV
EHHNLPDLMYRAFEVLPKMVMTPYTAFQKELHGETEEVYLEEMVGRVNANMILPYPPGVPLVMPGEMITEESRPVLEFLQMLC
EIGAHYPGFETDRIGAYRQADGRYTVKVLKENTK

What is claimed is:
1. A product, which is one of the following products I) through VI):
I) a CadA variant polypeptide comprising at least one amino acid substitution in a region corresponding to amino acids 455 to 483 as determined with reference to SEQ ID NO: 2, wherein the at least one amino acid substitution is at a histidine residue at position 458 and/or at an aspartic acid residue at position 457 and/or at an aspartate residue at position 460; and wherein the CadA variant polypeptide has at least 95% identity to any one of SEQ ID NOS: 2 to 5, wherein the at least one amino acid substitution at the histidine residue at position 458 is H458A/C/E/F/G/M/P/T/V/W/Y, the at least one amino acid substitution at the aspartic acid residue at position 457 is D457A/C/F/H/I/K/L/M/N/S/W/Y, and the at least one amino acid substitution at the aspartate residue at position 460 is D460F/ V/W/Y;
II) a polynucleotide comprising a nucleic acid sequence encoding a CadA variant polypeptide of I);
III) an expression vector comprising a polynucleotide of II);
IV) a genetically modified host cell comprising a CadA variant polypeptide of I);
V) a genetically modified host cell comprising a polynucleotide of II), wherein the nucleic acid sequence encoding the CadA variant polypeptide is integrated into the host cell chromosome; or
VI) a genetically modified host cell comprising an expression vector of III).
2. A product of claim 1, which is IV) the genetically modified host cell, wherein the host cell is genetically modified to over express one or more lysine biosynthesis polypeptides.
3. A product of claim 1, which is IV) the genetically modified host cell, wherein the host cell is a bacterium.
4. The product of claim 3, wherein the host cell is from the genus *Escherichia, Hafnia* or *Corynebacterium*.
5. The product of claim 3, wherein the host cell is selected from the group consisting of *Escherichia coli, Corynebacterium glutamicum* and *Hafnia alvei*.
6. A product of claim 1, which is V) the genetically modified host cell, wherein the host cell is a bacterium.
7. The product of claim 6, wherein the host cell is from the genus *Escherichia, Hafnia* or *Corynebacterium*.
8. The product of claim 6, wherein the host cell is selected from the group consisting of *Escherichia coli, Corynebacterium glutamicum* and *Hafnia alvei*.
9. A product of claim 1, which is VI) the genetically modified host cell, wherein the host cell is from the genus *Escherichia, Hafnia* or *Corynebacterium*.
10. The product of claim 9, wherein the host cell is selected from the group consisting of *Escherichia coli, Corynebacterium glutamicum* and *Hafnia alvei*.
11. A method, which is one of the following methods I) through III):
I) a method of producing cadaverine, the method comprising culturing a genetically modified host cell under conditions in which the CadA variant polypeptide is expressed, wherein the genetically modified host cell comprises a CadA variant polypeptide comprising at least one amino acid substitution in a region corresponding to amino acids 455 to 483 as determined with reference to SEQ ID NO: 2, wherein the at least one amino acid substitution is at a histidine residue at position 458 and/or at an aspartic acid residue at position 457 and/or at an aspartate residue at position 460; and the CadA variant polypeptide has at least 95% identity to any one of SEQ ID NOS: 2 to 5, wherein the at least one amino acid substitution at the histidine residue at position 458 is H458A/C/E/F/G/M/P/TN/W/ Y, the at least one amino acid substitution at the aspartic acid residue at position 457 is D457A/C/F/H/I/K/L/M/ N/S/W/Y, and the at least one amino acid substitution at the aspartate residue at position 460 is D460F/ V/W/Y;
II) a method of producing cadaverine, the method comprising culturing a genetically modified host cell under conditions in which the CadA variant polypeptide is expressed, wherein the genetically modified host cell comprises a polynucleotide comprising a nucleic acid sequence encoding a CadA variant polypeptide comprising at least one amino acid substitution in a region corresponding to amino acids 455 to 483 as determined with reference to SEQ ID NO: 2, wherein the at least one amino acid substitution is at a histidine residue at position 458 and/or at an aspartic acid residue at position 457 and/or at an aspartate residue at position 460; and the CadA variant polypeptide has at least 95% identity to any one of SEQ ID NOS: 2 to 5, wherein the nucleic acid sequence encoding the CadA variant polypeptide is integrated into the host cell chromosome, wherein the at least one amino acid substitution at the histidine residue at position 458 is H458A/C/E/F/G/M/ P/T/V/W/Y, the at least one amino acid substitution at the aspartic acid residue at position 457 is D457A/C/ F/H/I/K/L/M/N/S/W/Y, and the at least one amino acid substitution at the aspartate residue at position 460 is D460F/V/W/Y; or
III) a method of producing cadaverine, the method comprising culturing a genetically modified host cell under conditions in which the CadA variant polypeptide is expressed, wherein the genetically modified host cell comprises an expression vector comprising a polynucleotide comprising a nucleic acid sequence encoding a CadA variant polypeptide comprising at least one amino acid substitution in a region corresponding to amino acids 455 to 483 as determined with reference to SEQ ID NO: 2, wherein the at least one amino acid substitution is at a histidine residue at position 458 and/or at an aspartic acid residue at position 457 and/or at an aspartate residue at position 460; and the CadA variant polypeptide has at least 95% identity to any one of SEQ ID NOS: 2 to 5, wherein the at least one amino acid substitution at the histidine residue at position 458 is H458A/C/F/G/M/P/TN/W/Y, the at least one amino acid substitution at the aspartic acid residue at position 457 is D457A/C/F/H/I/K/L/M/N/S/W/Y, and the at least one amino acid substitution at the aspartate residue at position 460 is D460F/V/W/Y.
12. The method of claim 11, wherein, in I), II) or III), the host cell is a bacterium.
13. The method of claim 11, wherein, in I), II) or III), the host cell is from the genus *Escherichia, Hafnia* or *Corynebacterium*.
14. The method of claim 11, wherein, in I), II) or III), the host cell is selected from the group consisting of *Escherichia coli, Corynebacterium glutamicum* and *Hafnia alvei*.

* * * * *

SEQUENCE LISTING

<160> NUMBER OF SEQ ID NOS: 121

<210> SEQ ID NO 1
<211> LENGTH: 2148
<212> TYPE: DNA
<213> ORGANISM: Escherichia coli

<400> SEQUENCE: 1

| | | | | | |
|---|---|---|---|---|---|
| atgaacgtta | ttgcaatatt | gaatcacatg | ggggtttatt | ttaaagaaga | acccatccgt | 60 |
| gaacttcatc | gcgcgcttga | acgtctgaac | ttccagattg | tttacccgaa | cgaccgtgac | 120 |
| gacttattaa | aactgatcga | aaacaatgcg | cgtctgtgcg | gcgttatttt | tgactgggat | 180 |
| aaatataatc | tcgagctgtg | cgaagaaatt | agcaaaatga | acgagaacct | gccgttgtac | 240 |
| gcgttcgcta | atacgtattc | cactctcgat | gtaagcctga | atgacctgcg | tttacagatt | 300 |
| agcttctttg | aatatgcgct | gggtgctgct | gaagatattg | ctaataagat | caagcagacc | 360 |
| actgacgaat | atatcaacac | tattctgcct | ccgctgacta | agcactgtt | taaatatgtt | 420 |
| cgtgaaggta | aatatacttt | ctgtactcct | ggtcacatgg | gcggtactgc | attccagaaa | 480 |
| agcccggtag | gtagcctgtt | ctatgatttc | tttggtccga | ataccatgaa | atctgatatt | 540 |
| tccatttcag | tatctgaact | gggttctctg | ctggatcaca | gtggtccaca | caagaagca | 600 |
| gaacagtata | tcgctcgcgt | ctttaacgca | gaccgcagct | acatggtgac | aacggtact | 660 |
| tccactgcga | acaaaattgt | tggtatgtac | tctgctccag | caggcagcac | cattctgatt | 720 |
| gaccgtaact | gccacaaatc | gctgacccac | ctgatgatga | tgagcgatgt | tacgccaatc | 780 |
| tatttccgcc | cgacccgtaa | cgcttacggt | attcttggtg | gtatcccaca | gagtgaattc | 840 |
| cagcacgcta | ccattgctaa | gcgcgtgaaa | gaaacaccaa | acgcaacctg | gccggtacat | 900 |
| gctgtaatta | ccaactctac | ctatgatggt | ctgctgtaca | acaccgactt | catcaagaaa | 960 |
| acactggatg | tgaaatccat | ccactttgac | tccgcgtggg | tgccttacac | caacttctca | 1020 |
| ccgatttacg | aaggtaaatg | cggtatgagc | ggtggccgtg | tagaagggaa | agtgatttac | 1080 |
| gaaacccagt | ccactcacaa | actgctggcg | gcgttctctc | aggcttccat | gatccacgtt | 1140 |
| aaaggtgacg | taaacgaaga | aacctttaac | gaagcctaca | tgatgcacac | caccacttct | 1200 |
| ccgcactacg | gtatcgtggc | gtccactgaa | accgctgcgg | cgatgatgaa | aggcaatgca | 1260 |
| ggtaagcgtc | tgatcaacgg | ttctattgaa | cgtgcgatca | aattccgtaa | agagatcaaa | 1320 |
| cgtctgagaa | cggaatctga | tggctggttc | tttgatgtat | ggcagccgga | tcatatcgat | 1380 |
| acgactgaat | gctggccgct | gcgttctgac | agcacctggc | acggcttcaa | aaacatcgat | 1440 |
| aacgagcaca | tgtatcttga | cccgatcaaa | gtcaccctgc | tgactccggg | gatggaaaaa | 1500 |
| gacggcacca | tgagcgactt | tggtattccg | gccagcatcg | tggcgaaata | cctcgacgaa | 1560 |
| catggcatcg | ttgttgagaa | aaccggtccg | tataacctgc | tgttcctgtt | cagcatcggt | 1620 |
| atcgataaga | ccaaagcact | gagcctgctg | cgtgctctga | ctgactttaa | acgtgcgttc | 1680 |
| gacctgaacc | tgcgtgtgaa | aaacatgctg | ccgtctctgt | atcgtgaaga | tcctgaattc | 1740 |
| tatgaaaaca | tgcgtattca | ggaactggct | cagaatatcc | acaaactgat | tgttcaccac | 1800 |
| aatctgccgg | atctgatgta | tcgcgcattt | gaagtgctgc | cgacgatggt | aatgactccg | 1860 |
| tatgctgcat | tccagaaaga | gctgcacggt | atgaccgaag | aagtttacct | cgacgaaatg | 1920 |
| gtaggtcgta | ttaacgccaa | tatgatcctt | ccgtacccgc | cgggagttcc | tctggtaatg | 1980 |
| ccgggtgaaa | tgatcaccga | agaaagccgt | ccggttctgg | agttcctgca | gatgctgtgt | 2040 |
| gaaatcggcg | ctcactatcc | gggctttgaa | accgatattc | acggtgcata | ccgtcaggct | 2100 |

```
gatggccgct ataccgttaa ggtattgaaa gaagaaagca aaaaataa                    2148
```

<210> SEQ ID NO 2
<211> LENGTH: 715
<212> TYPE: PRT
<213> ORGANISM: Escherichia coli

<400> SEQUENCE: 2

```
Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365
```

Leu Ala Ala Phe Ser Gln Ala Ser Met Ile His Val Lys Gly Asp Val
    370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
        435                 440                 445

Trp Phe Phe Asp Val Trp Gln Pro Asp His Ile Asp Thr Thr Glu Cys
    450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
        515                 520                 525

Gly Pro Tyr Asn Leu Leu Phe Leu Phe Ser Ile Gly Ile Asp Lys Thr
    530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Ser Lys Lys
705                 710                 715

<210> SEQ ID NO 3
<211> LENGTH: 715
<212> TYPE: PRT
<213> ORGANISM: Klebsiella

<400> SEQUENCE: 3

Met Asn Val Ile Ala Ile Met Asn His Met Gly Val Tyr Phe Lys Glu
1               5                   10                  15

Glu Pro Ile Arg Glu Leu His Arg Ala Leu Glu Arg Leu Asp Phe Arg

```
                    20                  25                  30
Ile Val Tyr Pro Asn Asp Arg Asp Leu Leu Lys Leu Ile Glu Asn
            35                  40                  45

Asn Ser Arg Leu Cys Gly Val Ile Phe Asp Trp Asp Lys Tyr Asn Leu
    50                  55                  60

Glu Leu Cys Glu Glu Ile Ser Lys Met Asn Glu Tyr Met Pro Leu Tyr
65                      70                  75                  80

Ala Phe Ala Asn Thr Tyr Ser Thr Leu Asp Val Ser Leu Asn Asp Leu
                85                  90                  95

Arg Met Gln Val Arg Phe Phe Glu Tyr Ala Leu Gly Ala Ala Glu Asp
            100                 105                 110

Ile Ala Asn Lys Ile Lys Gln Asn Thr Asp Glu Tyr Ile Asp Thr Ile
            115                 120                 125

Leu Pro Pro Leu Thr Lys Ala Leu Phe Lys Tyr Val Arg Glu Gly Lys
            130                 135                 140

Tyr Thr Phe Cys Thr Pro Gly His Met Gly Gly Thr Ala Phe Gln Lys
145                 150                 155                 160

Ser Pro Val Gly Ser Ile Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Tyr Ile Ala Arg Val Phe
            195                 200                 205

Asn Ala Glu Arg Ser Tyr Met Val Thr Asn Gly Thr Ser Thr Ala Asn
            210                 215                 220

Lys Ile Val Gly Met Tyr Ser Ala Pro Ala Gly Ser Thr Val Leu Ile
225                 230                 235                 240

Asp Arg Asn Cys His Lys Ser Leu Thr His Leu Met Met Met Ser Asp
                245                 250                 255

Ile Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
            290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
            370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asp Gly Ser Ile Glu Arg Ser
            420                 425                 430

Ile Lys Phe Arg Lys Glu Ile Lys Arg Leu Lys Gly Glu Ser Asp Gly
            435                 440                 445
```

Trp Phe Asp Val Trp Gln Pro Glu His Ile Asp Gly Pro Glu Cys
450                 455                 460

Trp Pro Leu Arg Ser Asp Ser Ala Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Lys Lys Asp Gly Thr Met Asp Asp Phe Gly Ile Pro Ala Ser
                500                 505                 510

Ile Val Ala Lys Tyr Leu Asp Glu His Gly Ile Val Val Glu Lys Thr
                515                 520                 525

Gly Pro Tyr Asn Leu Leu Phe Leu Phe Ser Ile Gly Ile Asp Lys Thr
530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Asp Leu Ala Gln Asn
                580                 585                 590

Ile His Lys Leu Ile Glu His His Asn Leu Pro Asp Leu Met Phe Arg
                595                 600                 605

Ala Phe Glu Val Leu Pro Ser Met Val Met Thr Pro Tyr Ala Ala Phe
                610                 615                 620

Gln Lys Glu Leu His Gly Gln Thr Glu Glu Val Tyr Leu Glu Glu Met
625                 630                 635                 640

Val Gly Arg Val Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
                675                 680                 685

Phe Glu Thr Asp Ile His Gly Ala Tyr Arg Gln Ala Asp Gly Arg Tyr
                690                 695                 700

Thr Val Lys Val Leu Lys Glu Glu Asn Asn Lys
705                 710                 715

<210> SEQ ID NO 4
<211> LENGTH: 715
<212> TYPE: PRT
<213> ORGANISM: Enterobacteriaceae

<400> SEQUENCE: 4

Met Asn Val Ile Ala Ile Met Asn His Met Gly Val Tyr Phe Lys Glu
1               5                   10                  15

Glu Pro Ile Arg Glu Leu His Arg Ala Leu Glu Arg Leu Asp Phe Arg
                20                  25                  30

Ile Val Tyr Pro Asn Asp Arg Asp Asp Leu Leu Lys Leu Ile Glu Asn
                35                  40                  45

Asn Ser Arg Leu Cys Gly Val Ile Phe Asp Trp Asp Lys Tyr Asn Leu
                50                  55                  60

Glu Leu Cys Glu Glu Ile Ser Lys Met Asn Glu Tyr Met Pro Leu Tyr
65                  70                  75                  80

Ala Phe Ala Asn Thr Tyr Ser Thr Leu Asp Val Ser Leu Asn Asp Leu
                85                  90                  95

Arg Met Gln Val Arg Phe Phe Glu Tyr Ala Leu Gly Ala Ala Glu Asp

```
                100             105             110
Ile Ala Asn Lys Ile Lys Gln Asn Thr Asp Glu Tyr Ile Asp Thr Ile
            115             120             125
Leu Pro Pro Leu Thr Lys Ala Leu Phe Lys Tyr Val Arg Glu Gly Lys
            130             135             140
Tyr Thr Phe Cys Thr Pro Gly His Met Gly Thr Ala Phe Gln Lys
145             150             155             160
Ser Pro Val Gly Ser Ile Phe Tyr Asp Phe Gly Ser Asn Thr Met
                165             170             175
Lys Ser Asp Ile Ser Ile Ser Val Ser Glu Leu Gly Ser Leu Leu Asp
            180             185             190
His Ser Gly Pro His Lys Glu Ala Glu Tyr Ile Ala Arg Val Phe
            195             200             205
Asn Ala Glu Arg Ser Tyr Met Val Thr Asn Gly Thr Ser Thr Ala Asn
            210             215             220
Lys Ile Val Gly Met Tyr Ser Ala Pro Ala Gly Ser Thr Val Leu Ile
225             230             235             240
Asp Arg Asn Cys His Lys Ser Leu Thr His Leu Met Met Met Ser Asp
                245             250             255
Ile Thr Pro Ile Tyr Phe Arg Pro Thr Arg Asn Ala Tyr Gly Ile Leu
            260             265             270
Gly Gly Ile Pro Gln Ser Glu Phe Gln His Ala Thr Ile Ala Lys Arg
            275             280             285
Val Lys Glu Thr Pro Asn Ala Thr Trp Pro Val His Ala Val Ile Thr
            290             295             300
Asn Ser Thr Tyr Asp Gly Leu Leu Tyr Asn Thr Asp Phe Ile Lys Lys
305             310             315             320
Thr Leu Asp Val Lys Ser Ile His Phe Asp Ser Ala Trp Val Pro Tyr
                325             330             335
Thr Asn Phe Ser Pro Ile Tyr Glu Gly Lys Cys Gly Met Ser Gly Gly
            340             345             350
Arg Val Glu Gly Lys Val Ile Tyr Glu Thr Gln Ser Thr His Lys Leu
            355             360             365
Leu Ala Ala Phe Ser Gln Ala Ser Met Ile His Val Lys Gly Asp Val
            370             375             380
Asn Glu Glu Thr Phe Asn Glu Ala Tyr Met Met His Thr Thr Thr Ser
385             390             395             400
Pro His Tyr Gly Ile Val Ala Ser Thr Glu Thr Ala Ala Ala Met Met
                405             410             415
Lys Gly Asn Ala Gly Lys Arg Leu Ile Asp Gly Ser Ile Glu Arg Ser
            420             425             430
Ile Lys Phe Arg Lys Glu Ile Lys Arg Leu Lys Gly Glu Ser Asp Gly
            435             440             445
Trp Phe Phe Asp Val Trp Gln Pro Glu His Ile Asp Gly Pro Glu Cys
            450             455             460
Trp Pro Leu Arg Ser Asp Ser Ala Trp His Gly Phe Lys Asn Ile Asp
465             470             475             480
Asn Glu His Met Tyr Leu Asp Pro Ile Lys Val Thr Leu Leu Thr Pro
                485             490             495
Gly Met Lys Lys Asp Gly Thr Met Asp Asp Phe Gly Ile Pro Ala Ser
            500             505             510
Ile Val Ala Lys Tyr Leu Asp Glu His Gly Ile Val Val Glu Lys Thr
            515             520             525
```

```
Gly Pro Tyr Asn Leu Leu Phe Leu Phe Ser Ile Gly Ile Asp Lys Thr
            530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Asp Leu Ala Gln Asn
            580                 585                 590

Ile His Lys Leu Ile Glu His His Asn Leu Pro Asp Leu Met Phe Arg
            595                 600                 605

Ala Phe Glu Val Leu Pro Ser Met Val Met Thr Pro Tyr Ala Ala Phe
610                 615                 620

Gln Lys Glu Leu His Gly Gln Thr Glu Glu Val Tyr Leu Glu Glu Met
625                 630                 635                 640

Val Gly Arg Val Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
            690                 695                 700

Thr Val Lys Val Leu Lys Glu Glu Asn Asn Lys
705                 710                 715

<210> SEQ ID NO 5
<211> LENGTH: 714
<212> TYPE: PRT
<213> ORGANISM: Salmonella enterica

<400> SEQUENCE: 5

Met Asn Val Ile Ala Ile Met Asn His Met Gly Val Tyr Phe Lys Glu
1               5                   10                  15

Glu Pro Ile Arg Glu Leu His Arg Ala Leu Glu Gly Leu Asn Phe Arg
            20                  25                  30

Ile Val Tyr Pro Asn Asp Arg Glu Asp Leu Leu Lys Leu Ile Glu Asn
        35                  40                  45

Asn Ser Arg Leu Cys Gly Val Ile Phe Asp Trp Asp Lys Tyr Asn Leu
    50                  55                  60

Glu Leu Cys Glu Glu Ile Ser Lys Leu Asn Glu Tyr Met Pro Leu Tyr
65                  70                  75                  80

Ala Phe Ala Asn Ser Tyr Ser Thr Leu Asp Val Ser Leu Asn Asp Leu
                85                  90                  95

Arg Met Gln Val Arg Phe Phe Glu Tyr Ala Leu Gly Ala Ala Thr Asp
            100                 105                 110

Ile Ala Ala Lys Ile Arg Gln Asn Thr Asp Glu Tyr Ile Asp Asn Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Ile Phe Tyr Asp Phe Phe Gly Pro Asn Thr Met
                165                 170                 175

Lys Ser Asp Ile Ser Ile Ser Val Ser Glu Leu Gly Ser Leu Leu Asp
```

-continued

His Ser Gly Pro His Lys Glu Ala Glu Tyr Ile Ala Arg Val Phe
            180                 185                 190

Asn Ala Glu Arg Ser Tyr Met Val Thr Asn Gly Thr Ser Thr Ala Asn
195                 200                 205

Lys Ile Val Gly Met Tyr Ser Ala Pro Ala Gly Ser Thr Val Leu Ile
210                 215                 220

Asp Arg Asn Cys His Lys Ser Leu Thr His Leu Met Met Met Ser Asp
225                 230                 235                 240

Ile Thr Pro Ile Tyr Phe Arg Pro Thr Arg Asn Ala Tyr Gly Ile Leu
        245                 250                 255

Gly Gly Ile Pro Gln Ser Glu Phe Gln His Ala Thr Ile Ala Lys Arg
    260                 265                 270

Val Lys Glu Thr Pro Asn Ala Thr Trp Pro Val His Ala Val Ile Thr
275                 280                 285

Asn Ser Thr Tyr Asp Gly Leu Leu Tyr Asn Thr Asp Tyr Ile Lys Lys
290                 295                 300

Thr Leu Asp Val Lys Ser Ile His Phe Asp Ser Ala Trp Val Pro Tyr
305                 310                 315                 320

Thr Asn Phe Ser Pro Ile Tyr Gln Gly Lys Cys Gly Met Ser Gly Asp
        325                 330                 335

Arg Val Glu Gly Lys Ile Ile Tyr Glu Thr Gln Ser Thr His Lys Leu
    340                 345                 350

Leu Ala Ala Phe Ser Gln Ala Ser Met Ile His Val Lys Gly Asp Ile
355                 360                 365

Asn Glu Glu Thr Phe Asn Glu Ala Tyr Met Met His Thr Thr Thr Ser
370                 375                 380

Pro His Tyr Gly Ile Val Ala Ser Thr Glu Thr Ala Ala Ala Met Met
385                 390                 395                 400

Lys Gly Asn Ala Gly Lys Arg Leu Ile Asn Gly Ser Ile Glu Arg Ala
        405                 410                 415

Ile Lys Phe Arg Lys Glu Ile Lys Arg Leu Lys Ser Glu Ser Asp Gly
    420                 425                 430

Trp Phe Phe Asp Val Trp Gln Pro Glu His Ile Asp Gly Ala Glu Cys
435                 440                 445

Trp Pro Leu Arg Ser Asp Ser Ala Trp His Gly Phe Lys Asn Ile Asp
450                 455                 460

Asn Glu His Met Tyr Leu Asp Pro Ile Lys Val Thr Ile Leu Thr Pro
465                 470                 475                 480

Gly Met Lys Lys Asp Gly Thr Met Asp Glu Phe Gly Ile Pro Ala Ser
        485                 490                 495

Leu Val Ala Lys Tyr Leu Asp Glu Arg Gly Ile Ile Val Glu Lys Thr
    500                 505                 510

Gly Pro Tyr Asn Leu Leu Phe Leu Phe Ser Ile Gly Ile Asp Lys Thr
515                 520                 525

Lys Ala Leu Ser Leu Leu Arg Ala Leu Thr Glu Phe Lys Arg Ala Phe
530                 535                 540

Asp Leu Asn Leu Arg Val Lys Asn Ile Leu Pro Ala Leu Tyr Arg Glu
545                 550                 555                 560

Ala Pro Glu Phe Tyr Glu Asn Met Arg Ile Gln Glu Leu Ala Gln Asn
        565                 570                 575

Ile His Lys Leu Val Glu His His Asn Leu Pro Asp Leu Met Tyr Arg
    580                 585                 590

595                 600                 605

```
Ala Phe Glu Val Leu Pro Lys Met Val Met Thr Pro Tyr Thr Ala Phe
        610                 615                 620
Gln Lys Glu Leu His Gly Glu Thr Glu Glu Val Tyr Leu Glu Glu Met
625                 630                 635                 640
Val Gly Arg Val Asn Ala Asn Met Ile Leu Pro Tyr Pro Pro Gly Val
                645                 650                 655
Pro Leu Val Met Pro Gly Glu Met Ile Thr Glu Glu Ser Arg Pro Val
                660                 665                 670
Leu Glu Phe Leu Gln Met Leu Cys Glu Ile Gly Ala His Tyr Pro Gly
            675                 680                 685
Phe Glu Thr Asp Ile His Gly Ala Tyr Arg Gln Ala Asp Gly Arg Tyr
        690                 695                 700
Thr Val Lys Val Leu Lys Glu Asn Thr Lys
705                 710
```

<210> SEQ ID NO 6
<211> LENGTH: 52
<212> TYPE: DNA
<213> ORGANISM: Artificial Sequence
<220> FEATURE:
<223> OTHER INFORMATION: Primer cadA-F

<400> SEQUENCE: 6
ggcgagctca cacaggaaac agaccatgaa cgttattgca atattgaatc ac            52

<210> SEQ ID NO 7
<211> LENGTH: 28
<212> TYPE: DNA
<213> ORGANISM: Artificial Sequence
<220> FEATURE:
<223> OTHER INFORMATION: Primer cadA-R

<400> SEQUENCE: 7
ggctctagac cacttccctt gtacgagc                                       28

<210> SEQ ID NO 8
<211> LENGTH: 44
<212> TYPE: DNA
<213> ORGANISM: Artificial Sequence
<220> FEATURE:
<223> OTHER INFORMATION: Primer cadA-F2

<400> SEQUENCE: 8
atttcacaca ggaaacagct atgaacgtta ttgcaatatt gaat                    44

<210> SEQ ID NO 9
<211> LENGTH: 20
<212> TYPE: DNA
<213> ORGANISM: Artificial Sequence
<220> FEATURE:
<223> OTHER INFORMATION: Primer cadA-R2

<400> SEQUENCE: 9
agctgtttcc tgtgtgaaat                                                20

<210> SEQ ID NO 10
<211> LENGTH: 32
<212> TYPE: DNA
<213> ORGANISM: Artificial Sequence
<220> FEATURE:
<223> OTHER INFORMATION: Primer D457C-F

<400> SEQUENCE: 10
tggcagccgt gtcatatcga tacgactgaa tg                    32

<210> SEQ ID NO 11
<211> LENGTH: 31
<212> TYPE: DNA
<213> ORGANISM: Artificial Sequence
<220> FEATURE:
<223> OTHER INFORMATION: Primer D457C-R

<400> SEQUENCE: 11
atcgatatga cacggctgcc atacatcaaa g                    31

<210> SEQ ID NO 12
<211> LENGTH: 32
<212> TYPE: DNA
<213> ORGANISM: Artificial Sequence
<220> FEATURE:
<223> OTHER INFORMATION: Primer D457A-F

<400> SEQUENCE: 12
tggcagccgg cgcatatcga tacgactgaa tg                    32

<210> SEQ ID NO 13
<211> LENGTH: 31
<212> TYPE: DNA
<213> ORGANISM: Artificial Sequence
<220> FEATURE:
<223> OTHER INFORMATION: Primer D457A-R

<400> SEQUENCE: 13
atcgatatgc gccggctgcc atacatcaaa g                    31

<210> SEQ ID NO 14
<211> LENGTH: 32
<212> TYPE: DNA
<213> ORGANISM: Artificial Sequence
<220> FEATURE:
<223> OTHER INFORMATION: Primer D457H-F

<400> SEQUENCE: 14
tggcagccgc atcatatcga tacgactgaa tg                    32

<210> SEQ ID NO 15
<211> LENGTH: 31
<212> TYPE: DNA
<213> ORGANISM: Artificial Sequence
<220> FEATURE:
<223> OTHER INFORMATION: Primer D457H-R

<400> SEQUENCE: 15
atcgatatga tgcggctgcc atacatcaaa g                    31

<210> SEQ ID NO 16
<211> LENGTH: 32
<212> TYPE: DNA
<213> ORGANISM: Artificial Sequence
<220> FEATURE:
<223> OTHER INFORMATION: Primer D457K-F

<400> SEQUENCE: 16
tggcagccga aacatatcga tacgactgaa tg                    32

<210> SEQ ID NO 17
<211> LENGTH: 31
<212> TYPE: DNA

<213> ORGANISM: Artificial Sequence
<220> FEATURE:
<223> OTHER INFORMATION: Primer D457K-R

<400> SEQUENCE: 17
atcgatatgt tcggctgcc atacatcaaa g          31

<210> SEQ ID NO 18
<211> LENGTH: 32
<212> TYPE: DNA
<213> ORGANISM: Artificial Sequence
<220> FEATURE:
<223> OTHER INFORMATION: Primer D457R-F

<400> SEQUENCE: 18
tggcagccgc gtcatatcga tacgactgaa tg          32

<210> SEQ ID NO 19
<211> LENGTH: 31
<212> TYPE: DNA
<213> ORGANISM: Artificial Sequence
<220> FEATURE:
<223> OTHER INFORMATION: Primer D457R-R

<400> SEQUENCE: 19
atcgatatga cgcggctgcc atacatcaaa g          31

<210> SEQ ID NO 20
<211> LENGTH: 32
<212> TYPE: DNA
<213> ORGANISM: Artificial Sequence
<220> FEATURE:
<223> OTHER INFORMATION: Primer D457L-F

<400> SEQUENCE: 20
tggcagccgc tgcatatcga tacgactgaa tg          32

<210> SEQ ID NO 21
<211> LENGTH: 31
<212> TYPE: DNA
<213> ORGANISM: Artificial Sequence
<220> FEATURE:
<223> OTHER INFORMATION: Primer D457L-R

<400> SEQUENCE: 21
atcgatatgc agcggctgcc atacatcaaa g          31

<210> SEQ ID NO 22
<211> LENGTH: 32
<212> TYPE: DNA
<213> ORGANISM: Artificial Sequence
<220> FEATURE:
<223> OTHER INFORMATION: Primer D457S-F

<400> SEQUENCE: 22
tggcagccga gccatatcga tacgactgaa tg          32

<210> SEQ ID NO 23
<211> LENGTH: 31
<212> TYPE: DNA
<213> ORGANISM: Artificial Sequence
<220> FEATURE:
<223> OTHER INFORMATION: Primer D457S-R

<400> SEQUENCE: 23
atcgatatgg ctcggctgcc atacatcaaa g          31

<210> SEQ ID NO 24
<211> LENGTH: 32
<212> TYPE: DNA
<213> ORGANISM: Artificial Sequence
<220> FEATURE:
<223> OTHER INFORMATION: Primer D457P-F

<400> SEQUENCE: 24
tggcagccgc cgcatatcga tacgactgaa tg                              32

<210> SEQ ID NO 25
<211> LENGTH: 31
<212> TYPE: DNA
<213> ORGANISM: Artificial Sequence
<220> FEATURE:
<223> OTHER INFORMATION: Primer D457P-R

<400> SEQUENCE: 25
atcgatatgc ggcggctgcc atacatcaaa g                               31

<210> SEQ ID NO 26
<211> LENGTH: 32
<212> TYPE: DNA
<213> ORGANISM: Artificial Sequence
<220> FEATURE:
<223> OTHER INFORMATION: Primer D457E-F

<400> SEQUENCE: 26
tggcagccgg aacatatcga tacgactgaa tg                              32

<210> SEQ ID NO 27
<211> LENGTH: 31
<212> TYPE: DNA
<213> ORGANISM: Artificial Sequence
<220> FEATURE:
<223> OTHER INFORMATION: Primer D457E-R

<400> SEQUENCE: 27
atcgatatgt tccggctgcc atacatcaaa g                               31

<210> SEQ ID NO 28
<211> LENGTH: 32
<212> TYPE: DNA
<213> ORGANISM: Artificial Sequence
<220> FEATURE:
<223> OTHER INFORMATION: Primer D457T-F

<400> SEQUENCE: 28
tggcagccga cccatatcga tacgactgaa tg                              32

<210> SEQ ID NO 29
<211> LENGTH: 31
<212> TYPE: DNA
<213> ORGANISM: Artificial Sequence
<220> FEATURE:
<223> OTHER INFORMATION: Primer D457T-R

<400> SEQUENCE: 29
atcgatatgg gtcggctgcc atacatcaaa g                               31

<210> SEQ ID NO 30
<211> LENGTH: 32
<212> TYPE: DNA
<213> ORGANISM: Artificial Sequence
<220> FEATURE:

<223> OTHER INFORMATION: Primer D457Y-F

<400> SEQUENCE: 30
tggcagccgt atcatatcga tacgactgaa tg                32

<210> SEQ ID NO 31
<211> LENGTH: 31
<212> TYPE: DNA
<213> ORGANISM: Artificial Sequence
<220> FEATURE:
<223> OTHER INFORMATION: Primer D457Y-R

<400> SEQUENCE: 31
atcgatatga tacggctgcc atacatcaaa g                 31

<210> SEQ ID NO 32
<211> LENGTH: 32
<212> TYPE: DNA
<213> ORGANISM: Artificial Sequence
<220> FEATURE:
<223> OTHER INFORMATION: Primer D457G-F

<400> SEQUENCE: 32
tggcagccgg gccatatcga tacgactgaa tg                32

<210> SEQ ID NO 33
<211> LENGTH: 31
<212> TYPE: DNA
<213> ORGANISM: Artificial Sequence
<220> FEATURE:
<223> OTHER INFORMATION: Primer D457G-R

<400> SEQUENCE: 33
atcgatatgg cccggctgcc atacatcaaa g                 31

<210> SEQ ID NO 34
<211> LENGTH: 32
<212> TYPE: DNA
<213> ORGANISM: Artificial Sequence
<220> FEATURE:
<223> OTHER INFORMATION: Primer D457V-F

<400> SEQUENCE: 34
tggcagccgg tgcatatcga tacgactgaa tg                32

<210> SEQ ID NO 35
<211> LENGTH: 31
<212> TYPE: DNA
<213> ORGANISM: Artificial Sequence
<220> FEATURE:
<223> OTHER INFORMATION: Primer D457V-R

<400> SEQUENCE: 35
atcgatatgc accggctgcc atacatcaaa g                 31

<210> SEQ ID NO 36
<211> LENGTH: 32
<212> TYPE: DNA
<213> ORGANISM: Artificial Sequence
<220> FEATURE:
<223> OTHER INFORMATION: Primer D457F-F

<400> SEQUENCE: 36
tggcagccgt ttcatatcga tacgactgaa tg                32

```
<210> SEQ ID NO 37
<211> LENGTH: 31
<212> TYPE: DNA
<213> ORGANISM: Artificial Sequence
<220> FEATURE:
<223> OTHER INFORMATION: Primer D457F-R

<400> SEQUENCE: 37
atcgatatga aacggctgcc atacatcaaa g                              31

<210> SEQ ID NO 38
<211> LENGTH: 32
<212> TYPE: DNA
<213> ORGANISM: Artificial Sequence
<220> FEATURE:
<223> OTHER INFORMATION: Primer D457N-F

<400> SEQUENCE: 38
tggcagccga accatatcga tacgactgaa tg                             32

<210> SEQ ID NO 39
<211> LENGTH: 31
<212> TYPE: DNA
<213> ORGANISM: Artificial Sequence
<220> FEATURE:
<223> OTHER INFORMATION: Primer D457N-R

<400> SEQUENCE: 39
atcgatatgg ttcggctgcc atacatcaaa g                              31

<210> SEQ ID NO 40
<211> LENGTH: 32
<212> TYPE: DNA
<213> ORGANISM: Artificial Sequence
<220> FEATURE:
<223> OTHER INFORMATION: Primer D457Q-F

<400> SEQUENCE: 40
tggcagccgc agcatatcga tacgactgaa tg                             32

<210> SEQ ID NO 41
<211> LENGTH: 31
<212> TYPE: DNA
<213> ORGANISM: Artificial Sequence
<220> FEATURE:
<223> OTHER INFORMATION: Primer D457Q-R

<400> SEQUENCE: 41
atcgatatgc tgcggctgcc atacatcaaa g                              31

<210> SEQ ID NO 42
<211> LENGTH: 32
<212> TYPE: DNA
<213> ORGANISM: Artificial Sequence
<220> FEATURE:
<223> OTHER INFORMATION: Primer D457I-F

<400> SEQUENCE: 42
tggcagccga tccatatcga tacgactgaa tg                             32

<210> SEQ ID NO 43
<211> LENGTH: 31
<212> TYPE: DNA
<213> ORGANISM: Artificial Sequence
<220> FEATURE:
<223> OTHER INFORMATION: Primer D457I-R
```

```
<400> SEQUENCE: 43
atcgatatgg atcggctgcc atacatcaaa g                                    31

<210> SEQ ID NO 44
<211> LENGTH: 32
<212> TYPE: DNA
<213> ORGANISM: Artificial Sequence
<220> FEATURE:
<223> OTHER INFORMATION: Primer D457M-F

<400> SEQUENCE: 44
tggcagccga tgcatatcga tacgactgaa tg                                   32

<210> SEQ ID NO 45
<211> LENGTH: 31
<212> TYPE: DNA
<213> ORGANISM: Artificial Sequence
<220> FEATURE:
<223> OTHER INFORMATION: Primer D457M-R

<400> SEQUENCE: 45
atcgatatgc atcggctgcc atacatcaaa g                                    31

<210> SEQ ID NO 46
<211> LENGTH: 32
<212> TYPE: DNA
<213> ORGANISM: Artificial Sequence
<220> FEATURE:
<223> OTHER INFORMATION: Primer D457W-F

<400> SEQUENCE: 46
tggcagccgt ggcatatcga tacgactgaa tg                                   32

<210> SEQ ID NO 47
<211> LENGTH: 31
<212> TYPE: DNA
<213> ORGANISM: Artificial Sequence
<220> FEATURE:
<223> OTHER INFORMATION: Primer D457W-R

<400> SEQUENCE: 47
atcgatatgc cacggctgcc atacatcaaa g                                    31

<210> SEQ ID NO 48
<211> LENGTH: 39
<212> TYPE: DNA
<213> ORGANISM: Artificial Sequence
<220> FEATURE:
<223> OTHER INFORMATION: Primer D460C-F

<400> SEQUENCE: 48
ggatcatatc tgcacgactg aatgctggcc gctgcgttc                            39

<210> SEQ ID NO 49
<211> LENGTH: 39
<212> TYPE: DNA
<213> ORGANISM: Artificial Sequence
<220> FEATURE:
<223> OTHER INFORMATION: Primer D460C-R

<400> SEQUENCE: 49
attcagtcgt gcagatatga tccggctgcc atacatcaa                            39

<210> SEQ ID NO 50
<211> LENGTH: 39
```

```
<212> TYPE: DNA
<213> ORGANISM: Artificial Sequence
<220> FEATURE:
<223> OTHER INFORMATION: Primer D460H-F

<400> SEQUENCE: 50
ggatcatatc catacgactg aatgctggcc gctgcgttc                              39

<210> SEQ ID NO 51
<211> LENGTH: 39
<212> TYPE: DNA
<213> ORGANISM: Artificial Sequence
<220> FEATURE:
<223> OTHER INFORMATION: Primer D460H-R

<400> SEQUENCE: 51
attcagtcgt atggatatga tccggctgcc atacatcaa                              39

<210> SEQ ID NO 52
<211> LENGTH: 39
<212> TYPE: DNA
<213> ORGANISM: Artificial Sequence
<220> FEATURE:
<223> OTHER INFORMATION: Primer D460K-F

<400> SEQUENCE: 52
ggatcatatc aaaacgactg aatgctggcc gctgcgttc                              39

<210> SEQ ID NO 53
<211> LENGTH: 39
<212> TYPE: DNA
<213> ORGANISM: Artificial Sequence
<220> FEATURE:
<223> OTHER INFORMATION: Primer D460K-R

<400> SEQUENCE: 53
attcagtcgt tttgatatga tccggctgcc atacatcaa                              39

<210> SEQ ID NO 54
<211> LENGTH: 39
<212> TYPE: DNA
<213> ORGANISM: Artificial Sequence
<220> FEATURE:
<223> OTHER INFORMATION: Primer D460R-F

<400> SEQUENCE: 54
ggatcatatc cgtacgactg aatgctggcc gctgcgttc                              39

<210> SEQ ID NO 55
<211> LENGTH: 39
<212> TYPE: DNA
<213> ORGANISM: Artificial Sequence
<220> FEATURE:
<223> OTHER INFORMATION: Primer D460R-R

<400> SEQUENCE: 55
attcagtcgt acggatatga tccggctgcc atacatcaa                              39

<210> SEQ ID NO 56
<211> LENGTH: 39
<212> TYPE: DNA
<213> ORGANISM: Artificial Sequence
<220> FEATURE:
<223> OTHER INFORMATION: Primer D460L-F

<400> SEQUENCE: 56
```
ggatcatatc ctgacgactg aatgctggcc gctgcgttc                           39

<210> SEQ ID NO 57
<211> LENGTH: 39
<212> TYPE: DNA
<213> ORGANISM: Artificial Sequence
<220> FEATURE:
<223> OTHER INFORMATION: Primer D460L-R

<400> SEQUENCE: 57
attcagtcgt caggatatga tccggctgcc atacatcaa                           39

<210> SEQ ID NO 58
<211> LENGTH: 39
<212> TYPE: DNA
<213> ORGANISM: Artificial Sequence
<220> FEATURE:
<223> OTHER INFORMATION: Primer D460S-F

<400> SEQUENCE: 58
ggatcatatc agcacgactg aatgctggcc gctgcgttc                           39

<210> SEQ ID NO 59
<211> LENGTH: 39
<212> TYPE: DNA
<213> ORGANISM: Artificial Sequence
<220> FEATURE:
<223> OTHER INFORMATION: Primer D460S-R

<400> SEQUENCE: 59
attcagtcgt gctgatatga tccggctgcc atacatcaa                           39

<210> SEQ ID NO 60
<211> LENGTH: 39
<212> TYPE: DNA
<213> ORGANISM: Artificial Sequence
<220> FEATURE:
<223> OTHER INFORMATION: Primer D460P-F

<400> SEQUENCE: 60
ggatcatatc ccgacgactg aatgctggcc gctgcgttc                           39

<210> SEQ ID NO 61
<211> LENGTH: 39
<212> TYPE: DNA
<213> ORGANISM: Artificial Sequence
<220> FEATURE:
<223> OTHER INFORMATION: Primer D460P-R

<400> SEQUENCE: 61
attcagtcgt cgggatatga tccggctgcc atacatcaa                           39

<210> SEQ ID NO 62
<211> LENGTH: 39
<212> TYPE: DNA
<213> ORGANISM: Artificial Sequence
<220> FEATURE:
<223> OTHER INFORMATION: Primer D460E-F

<400> SEQUENCE: 62
ggatcatatc gaaacgactg aatgctggcc gctgcgttc                           39

<210> SEQ ID NO 63
<211> LENGTH: 39
<212> TYPE: DNA
<213> ORGANISM: Artificial Sequence
<220> FEATURE:
<223> OTHER INFORMATION: Primer D460E-R

<400> SEQUENCE: 63
attcagtcgt ttcgatatga tccggctgcc atacatcaa            39

<210> SEQ ID NO 64
<211> LENGTH: 39
<212> TYPE: DNA
<213> ORGANISM: Artificial Sequence
<220> FEATURE:
<223> OTHER INFORMATION: Primer D460T-F

<400> SEQUENCE: 64
ggatcatatc accacgactg aatgctggcc gctgcgttc            39

<210> SEQ ID NO 65
<211> LENGTH: 39
<212> TYPE: DNA
<213> ORGANISM: Artificial Sequence
<220> FEATURE:
<223> OTHER INFORMATION: Primer D460T-R

<400> SEQUENCE: 65
attcagtcgt ggtgatatga tccggctgcc atacatcaa            39

<210> SEQ ID NO 66
<211> LENGTH: 39
<212> TYPE: DNA
<213> ORGANISM: Artificial Sequence
<220> FEATURE:
<223> OTHER INFORMATION: Primer D460Y-F

<400> SEQUENCE: 66
ggatcatatc tatacgactg aatgctggcc gctgcgttc            39

<210> SEQ ID NO 67
<211> LENGTH: 39
<212> TYPE: DNA
<213> ORGANISM: Artificial Sequence
<220> FEATURE:
<223> OTHER INFORMATION: Primer D460Y-R

<400> SEQUENCE: 67
attcagtcgt atagatatga tccggctgcc atacatcaa            39

<210> SEQ ID NO 68
<211> LENGTH: 39
<212> TYPE: DNA
<213> ORGANISM: Artificial Sequence
<220> FEATURE:
<223> OTHER INFORMATION: Primer D460A-F

<400> SEQUENCE: 68
ggatcatatc gcgacgactg aatgctggcc gctgcgttc            39

<210> SEQ ID NO 69
<211> LENGTH: 39
<212> TYPE: DNA
<213> ORGANISM: Artificial Sequence
<220> FEATURE:
<223> OTHER INFORMATION: Primer D460A-R

<400> SEQUENCE: 69
attcagtcgt cgcgatatga tccggctgcc atacatcaa            39

<210> SEQ ID NO 70
<211> LENGTH: 39
<212> TYPE: DNA
<213> ORGANISM: Artificial Sequence
<220> FEATURE:
<223> OTHER INFORMATION: Primer D460G-F

<400> SEQUENCE: 70
ggatcatatc ggcacgactg aatgctggcc gctgcgttc         39

<210> SEQ ID NO 71
<211> LENGTH: 39
<212> TYPE: DNA
<213> ORGANISM: Artificial Sequence
<220> FEATURE:
<223> OTHER INFORMATION: Primer D460G-R

<400> SEQUENCE: 71
attcagtcgt gccgatatga tccggctgcc atacatcaa         39

<210> SEQ ID NO 72
<211> LENGTH: 39
<212> TYPE: DNA
<213> ORGANISM: Artificial Sequence
<220> FEATURE:
<223> OTHER INFORMATION: Primer D460V-F

<400> SEQUENCE: 72
ggatcatatc gtgacgactg aatgctggcc gctgcgttc         39

<210> SEQ ID NO 73
<211> LENGTH: 39
<212> TYPE: DNA
<213> ORGANISM: Artificial Sequence
<220> FEATURE:
<223> OTHER INFORMATION: Primer D460V-R

<400> SEQUENCE: 73
attcagtcgt cacgatatga tccggctgcc atacatcaa         39

<210> SEQ ID NO 74
<211> LENGTH: 39
<212> TYPE: DNA
<213> ORGANISM: Artificial Sequence
<220> FEATURE:
<223> OTHER INFORMATION: Primer D460F-F

<400> SEQUENCE: 74
ggatcatatc tttacgactg aatgctggcc gctgcgttc         39

<210> SEQ ID NO 75
<211> LENGTH: 39
<212> TYPE: DNA
<213> ORGANISM: Artificial Sequence
<220> FEATURE:
<223> OTHER INFORMATION: Primer D460F-R

<400> SEQUENCE: 75
attcagtcgt aaagatatga tccggctgcc atacatcaa         39

<210> SEQ ID NO 76
<211> LENGTH: 39
<212> TYPE: DNA
<213> ORGANISM: Artificial Sequence
<220> FEATURE:
<223> OTHER INFORMATION: Primer D460N-F

<400> SEQUENCE: 76
ggatcatatc aacacgactg aatgctggcc gctgcgttc                    39

<210> SEQ ID NO 77
<211> LENGTH: 39
<212> TYPE: DNA
<213> ORGANISM: Artificial Sequence
<220> FEATURE:
<223> OTHER INFORMATION: Primer D460N-R

<400> SEQUENCE: 77
attcagtcgt gttgatatga tccggctgcc atacatcaa                    39

<210> SEQ ID NO 78
<211> LENGTH: 39
<212> TYPE: DNA
<213> ORGANISM: Artificial Sequence
<220> FEATURE:
<223> OTHER INFORMATION: Primer D460Q-F

<400> SEQUENCE: 78
ggatcatatc cagacgactg aatgctggcc gctgcgttc                    39

<210> SEQ ID NO 79
<211> LENGTH: 39
<212> TYPE: DNA
<213> ORGANISM: Artificial Sequence
<220> FEATURE:
<223> OTHER INFORMATION: Primer D460Q-R

<400> SEQUENCE: 79
attcagtcgt ctggatatga tccggctgcc atacatcaa                    39

<210> SEQ ID NO 80
<211> LENGTH: 39
<212> TYPE: DNA
<213> ORGANISM: Artificial Sequence
<220> FEATURE:
<223> OTHER INFORMATION: Primer D460I-F

<400> SEQUENCE: 80
ggatcatatc atcacgactg aatgctggcc gctgcgttc                    39

<210> SEQ ID NO 81
<211> LENGTH: 39
<212> TYPE: DNA
<213> ORGANISM: Artificial Sequence
<220> FEATURE:
<223> OTHER INFORMATION: Primer D460I-R

<400> SEQUENCE: 81
attcagtcgt gatgatatga tccggctgcc atacatcaa                    39

<210> SEQ ID NO 82
<211> LENGTH: 39
<212> TYPE: DNA
<213> ORGANISM: Artificial Sequence
<220> FEATURE:
<223> OTHER INFORMATION: Primer D460M-F

<400> SEQUENCE: 82
ggatcatatc atgacgactg aatgctggcc gctgcgttc                    39

<210> SEQ ID NO 83

```
<211> LENGTH: 39
<212> TYPE: DNA
<213> ORGANISM: Artificial Sequence
<220> FEATURE:
<223> OTHER INFORMATION: Primer D460M-R

<400> SEQUENCE: 83
attcagtcgt catgatatga tccggctgcc atacatcaa                    39

<210> SEQ ID NO 84
<211> LENGTH: 39
<212> TYPE: DNA
<213> ORGANISM: Artificial Sequence
<220> FEATURE:
<223> OTHER INFORMATION: Primer D460W-F

<400> SEQUENCE: 84
ggatcatatc tggacgactg aatgctggcc gctgcgttc                    39

<210> SEQ ID NO 85
<211> LENGTH: 39
<212> TYPE: DNA
<213> ORGANISM: Artificial Sequence
<220> FEATURE:
<223> OTHER INFORMATION: Primer D460W-R

<400> SEQUENCE: 85
attcagtcgt ccagatatga tccggctgcc atacatcaa                    39

<210> SEQ ID NO 86
<211> LENGTH: 36
<212> TYPE: DNA
<213> ORGANISM: Artificial Sequence
<220> FEATURE:
<223> OTHER INFORMATION: Primer H458F-F

<400> SEQUENCE: 86
atggcagccg gatttcatcg atacgactga atgctg                       36

<210> SEQ ID NO 87
<211> LENGTH: 40
<212> TYPE: DNA
<213> ORGANISM: Artificial Sequence
<220> FEATURE:
<223> OTHER INFORMATION: Primer H458F-R

<400> SEQUENCE: 87
agtcgtatcg atgaaatccg gctgccatac atcaaagaac                   40

<210> SEQ ID NO 88
<211> LENGTH: 36
<212> TYPE: DNA
<213> ORGANISM: Artificial Sequence
<220> FEATURE:
<223> OTHER INFORMATION: Primer H458L-F

<400> SEQUENCE: 88
atggcagccg gatctaatcg atacgactga atgctg                       36

<210> SEQ ID NO 89
<211> LENGTH: 40
<212> TYPE: DNA
<213> ORGANISM: Artificial Sequence
<220> FEATURE:
<223> OTHER INFORMATION: Primer H458L-R

<400> SEQUENCE: 89
```
agtcgtatcg attagatccg gctgccatac atcaaagaac                 40

<210> SEQ ID NO 90
<211> LENGTH: 36
<212> TYPE: DNA
<213> ORGANISM: Artificial Sequence
<220> FEATURE:
<223> OTHER INFORMATION: Primer H458S-F

<400> SEQUENCE: 90
atggcagccg gattgaatcg atacgactga atgctg                    36

<210> SEQ ID NO 91
<211> LENGTH: 40
<212> TYPE: DNA
<213> ORGANISM: Artificial Sequence
<220> FEATURE:
<223> OTHER INFORMATION: Primer H458S-R

<400> SEQUENCE: 91
agtcgtatcg attcaatccg gctgccatac atcaaagaac                 40

<210> SEQ ID NO 92
<211> LENGTH: 36
<212> TYPE: DNA
<213> ORGANISM: Artificial Sequence
<220> FEATURE:
<223> OTHER INFORMATION: Primer H458Y-F

<400> SEQUENCE: 92
atggcagccg gattacatcg atacgactga atgctg                    36

<210> SEQ ID NO 93
<211> LENGTH: 40
<212> TYPE: DNA
<213> ORGANISM: Artificial Sequence
<220> FEATURE:
<223> OTHER INFORMATION: Primer H458Y-R

<400> SEQUENCE: 93
agtcgtatcg atgtaatccg gctgccatac atcaaagaac                 40

<210> SEQ ID NO 94
<211> LENGTH: 36
<212> TYPE: DNA
<213> ORGANISM: Artificial Sequence
<220> FEATURE:
<223> OTHER INFORMATION: Primer H458P-F

<400> SEQUENCE: 94
atggcagccg gatccaatcg atacgactga atgctg                    36

<210> SEQ ID NO 95
<211> LENGTH: 40
<212> TYPE: DNA
<213> ORGANISM: Artificial Sequence
<220> FEATURE:
<223> OTHER INFORMATION: Primer H458P-R

<400> SEQUENCE: 95
agtcgtatcg attggatccg gctgccatac atcaaagaac                 40

<210> SEQ ID NO 96
<211> LENGTH: 36
<212> TYPE: DNA

<213> ORGANISM: Artificial Sequence
<220> FEATURE:
<223> OTHER INFORMATION: Primer H458Q-F

<400> SEQUENCE: 96
atggcagccg gatcaaatcg atacgactga atgctg                              36

<210> SEQ ID NO 97
<211> LENGTH: 40
<212> TYPE: DNA
<213> ORGANISM: Artificial Sequence
<220> FEATURE:
<223> OTHER INFORMATION: Primer H458Q-R

<400> SEQUENCE: 97
agtcgtatcg atttgatccg gctgccatac atcaaagaac                          40

<210> SEQ ID NO 98
<211> LENGTH: 36
<212> TYPE: DNA
<213> ORGANISM: Artificial Sequence
<220> FEATURE:
<223> OTHER INFORMATION: Primer H458R-F

<400> SEQUENCE: 98
atggcagccg gatcgtatcg atacgactga atgctg                              36

<210> SEQ ID NO 99
<211> LENGTH: 40
<212> TYPE: DNA
<213> ORGANISM: Artificial Sequence
<220> FEATURE:
<223> OTHER INFORMATION: Primer H458R-R

<400> SEQUENCE: 99
agtcgtatcg atacgatccg gctgccatac atcaaagaac                          40

<210> SEQ ID NO 100
<211> LENGTH: 36
<212> TYPE: DNA
<213> ORGANISM: Artificial Sequence
<220> FEATURE:
<223> OTHER INFORMATION: Primer H458W-F

<400> SEQUENCE: 100
atggcagccg gattggatcg atacgactga atgctg                              36

<210> SEQ ID NO 101
<211> LENGTH: 40
<212> TYPE: DNA
<213> ORGANISM: Artificial Sequence
<220> FEATURE:
<223> OTHER INFORMATION: Primer H458W-R

<400> SEQUENCE: 101
agtcgtatcg atccaatccg gctgccatac atcaaagaac                          40

<210> SEQ ID NO 102
<211> LENGTH: 36
<212> TYPE: DNA
<213> ORGANISM: Artificial Sequence
<220> FEATURE:
<223> OTHER INFORMATION: Primer H458I-F

<400> SEQUENCE: 102
atggcagccg gatatcatcg atacgactga atgctg                              36

<210> SEQ ID NO 103
<211> LENGTH: 40
<212> TYPE: DNA
<213> ORGANISM: Artificial Sequence
<220> FEATURE:
<223> OTHER INFORMATION: Primer H458I-R

<400> SEQUENCE: 103
agtcgtatcg atgatatccg gctgccatac atcaaagaac					40

<210> SEQ ID NO 104
<211> LENGTH: 36
<212> TYPE: DNA
<213> ORGANISM: Artificial Sequence
<220> FEATURE:
<223> OTHER INFORMATION: Primer H458T-F

<400> SEQUENCE: 104
atggcagccg gatactatcg atacgactga atgctg					36

<210> SEQ ID NO 105
<211> LENGTH: 40
<212> TYPE: DNA
<213> ORGANISM: Artificial Sequence
<220> FEATURE:
<223> OTHER INFORMATION: Primer H458T-R

<400> SEQUENCE: 105
agtcgtatcg atagtatccg gctgccatac atcaaagaac					40

<210> SEQ ID NO 106
<211> LENGTH: 36
<212> TYPE: DNA
<213> ORGANISM: Artificial Sequence
<220> FEATURE:
<223> OTHER INFORMATION: Primer H458D-F

<400> SEQUENCE: 106
atggcagccg gatgatatcg atacgactga atgctg					36

<210> SEQ ID NO 107
<211> LENGTH: 40
<212> TYPE: DNA
<213> ORGANISM: Artificial Sequence
<220> FEATURE:
<223> OTHER INFORMATION: Primer H458D-R

<400> SEQUENCE: 107
agtcgtatcg atatcatccg gctgccatac atcaaagaac					40

<210> SEQ ID NO 108
<211> LENGTH: 36
<212> TYPE: DNA
<213> ORGANISM: Artificial Sequence
<220> FEATURE:
<223> OTHER INFORMATION: Primer H458K-F

<400> SEQUENCE: 108
atggcagccg gataagatcg atacgactga atgctg					36

<210> SEQ ID NO 109
<211> LENGTH: 40
<212> TYPE: DNA
<213> ORGANISM: Artificial Sequence
<220> FEATURE:

<223> OTHER INFORMATION: Primer H458K-R

<400> SEQUENCE: 109
agtcgtatcg atcttatccg gctgccatac atcaaagaac                    40

<210> SEQ ID NO 110
<211> LENGTH: 36
<212> TYPE: DNA
<213> ORGANISM: Artificial Sequence
<220> FEATURE:
<223> OTHER INFORMATION: Primer H458N-F

<400> SEQUENCE: 110
atggcagccg gataacatcg atacgactga atgctg                        36

<210> SEQ ID NO 111
<211> LENGTH: 40
<212> TYPE: DNA
<213> ORGANISM: Artificial Sequence
<220> FEATURE:
<223> OTHER INFORMATION: Primer H458N-R

<400> SEQUENCE: 111
agtcgtatcg atgttatccg gctgccatac atcaaagaac                    40

<210> SEQ ID NO 112
<211> LENGTH: 36
<212> TYPE: DNA
<213> ORGANISM: Artificial Sequence
<220> FEATURE:
<223> OTHER INFORMATION: Primer H458E-F

<400> SEQUENCE: 112
atggcagccg gatgaaatcg atacgactga atgctg                        36

<210> SEQ ID NO 113
<211> LENGTH: 40
<212> TYPE: DNA
<213> ORGANISM: Artificial Sequence
<220> FEATURE:
<223> OTHER INFORMATION: Primer H458E-R

<400> SEQUENCE: 113
agtcgtatcg atttcatccg gctgccatac atcaaagaac                    40

<210> SEQ ID NO 114
<211> LENGTH: 36
<212> TYPE: DNA
<213> ORGANISM: Artificial Sequence
<220> FEATURE:
<223> OTHER INFORMATION: Primer H458A-F

<400> SEQUENCE: 114
atggcagccg gatgctatcg atacgactga atgctg                        36

<210> SEQ ID NO 115
<211> LENGTH: 40
<212> TYPE: DNA
<213> ORGANISM: Artificial Sequence
<220> FEATURE:
<223> OTHER INFORMATION: Primer H458A-R

<400> SEQUENCE: 115
agtcgtatcg atagcatccg gctgccatac atcaaagaac                    40

<210> SEQ ID NO 116
<211> LENGTH: 36
<212> TYPE: DNA
<213> ORGANISM: Artificial Sequence
<220> FEATURE:
<223> OTHER INFORMATION: Primer H458G-F

<400> SEQUENCE: 116
atggcagccg gatggtatcg atacgactga atgctg         36

<210> SEQ ID NO 117
<211> LENGTH: 40
<212> TYPE: DNA
<213> ORGANISM: Artificial Sequence
<220> FEATURE:
<223> OTHER INFORMATION: Primer H458G-R

<400> SEQUENCE: 117
agtcgtatcg ataccatccg gctgccatac atcaaagaac         40

<210> SEQ ID NO 118
<211> LENGTH: 36
<212> TYPE: DNA
<213> ORGANISM: Artificial Sequence
<220> FEATURE:
<223> OTHER INFORMATION: Primer H458V-F

<400> SEQUENCE: 118
atggcagccg gatgtaatcg atacgactga atgctg         36

<210> SEQ ID NO 119
<211> LENGTH: 40
<212> TYPE: DNA
<213> ORGANISM: Artificial Sequence
<220> FEATURE:
<223> OTHER INFORMATION: Primer H458V-R

<400> SEQUENCE: 119
agtcgtatcg attacatccg gctgccatac atcaaagaac         40

<210> SEQ ID NO 120
<211> LENGTH: 36
<212> TYPE: DNA
<213> ORGANISM: Artificial Sequence
<220> FEATURE:
<223> OTHER INFORMATION: Primer H458M-F

<400> SEQUENCE: 120
atggcagccg gatatgatcg atacgactga atgctg         36

<210> SEQ ID NO 121
<211> LENGTH: 40
<212> TYPE: DNA
<213> ORGANISM: Artificial Sequence
<220> FEATURE:
<223> OTHER INFORMATION: Primer H458M-R

<400> SEQUENCE: 121
agtcgtatcg atcatatccg gctgccatac atcaaagaac         40